(12) United States Patent
Slomczynska et al.

(10) Patent No.: US 9,232,800 B2
(45) Date of Patent: Jan. 12, 2016

(54) 3,5-DISUBSTITUTED-4,5-DIHYDRO-1,2,4-OXADIAZOLES AND COMPOSITIONS AND METHODS FOR CONTROLLING NEMATODE PESTS

(71) Applicant: Monsanto Technology LLC, St. Louis, MO (US)

(72) Inventors: Urszula J. Slomczynska, Ballwin, MO (US); William P. Haakenson, St. Louis, MO (US)

(73) Assignee: Monsanto Technology LLC, St. Louis, MI (US)

( * ) Notice: Subject to any disclaimer, the term of this patent is extended or adjusted under 35 U.S.C. 154(b) by 0 days.

(21) Appl. No.: 14/180,629

(22) Filed: Feb. 14, 2014

(65) Prior Publication Data

US 2014/0235439 A1    Aug. 21, 2014

Related U.S. Application Data

(60) Provisional application No. 61/788,020, filed on Mar. 15, 2013, provisional application No. 61/765,477, filed on Feb. 15, 2013.

(51) Int. Cl.
| | |
|---|---|
| *C07D 407/04* | (2006.01) |
| *C07D 409/04* | (2006.01) |
| *A01N 43/82* | (2006.01) |
| *C07D 271/06* | (2006.01) |

(52) U.S. Cl.
CPC .............. *A01N 43/82* (2013.01); *C07D 271/06* (2013.01); *C07D 407/04* (2013.01); *C07D 409/04* (2013.01)

(58) Field of Classification Search
CPC ... C07D 407/04; C07D 409/04; C07D 271/06
USPC ........................................................ 548/131
See application file for complete search history.

(56) References Cited

U.S. PATENT DOCUMENTS

| | | | |
|---|---|---|---|
| 3,083,206 | A | 3/1963 | Von Esch et al. |
| 4,465,017 | A | 8/1984 | Simmons |
| 4,759,945 | A | 7/1988 | Nemecek et al. |
| 5,080,925 | A | 1/1992 | Kouno |
| 5,107,787 | A | 4/1992 | Kouno |
| 5,389,399 | A | 2/1995 | Bazin et al. |
| 5,554,445 | A | 9/1996 | Struszczyk et al. |
| 5,891,246 | A | 4/1999 | Lund |
| 5,918,413 | A | 7/1999 | Otani et al. |
| 5,981,565 | A | 11/1999 | Wu |
| 5,985,904 | A | 11/1999 | Jeschke et al. |
| 6,008,353 | A | 12/1999 | Wu |
| 6,107,314 | A | 8/2000 | Wu |
| 6,277,848 | B1 | 8/2001 | Wu |
| 6,346,522 | B1 | 2/2002 | Wu |
| 6,376,520 | B1 | 4/2002 | Wu |
| 6,432,997 | B1 | 8/2002 | Wu |
| 6,500,848 | B2 | 12/2002 | Wu |
| 6,593,328 | B2 | 7/2003 | Wu |
| 7,112,595 | B2 | 9/2006 | Wagenen et al. |
| 8,017,555 | B2 | 9/2011 | Slomczynska et al. |
| 8,435,999 | B2 | 5/2013 | Williams et al. |
| 2002/0173492 | A1 | 11/2002 | Wu |
| 2003/0013612 | A1 | 1/2003 | Asrar et al. |
| 2003/0092680 | A1 | 5/2003 | Wu |
| 2004/0097372 | A1 | 5/2004 | Abraham et al. |
| 2009/0165166 | A1 | 6/2009 | Feng et al. |
| 2013/0303368 | A1 | 11/2013 | Slomczynska et al. |

FOREIGN PATENT DOCUMENTS

| | | |
|---|---|---|
| EP | 0911329 A1 | 4/1999 |
| WO | 0112627 A1 | 2/2001 |
| WO | 2009023721 A1 | 2/2009 |
| WO | 2009055514 A2 | 4/2009 |
| WO | 2010093650 A2 | 8/2010 |
| WO | 2012030887 A1 | 3/2012 |

OTHER PUBLICATIONS

Gregory, et al. Document No. 150:554526, retrieved from CAPLUS; Jun. 12, 2009.*
Gregory, et al. Document No. 150:554525, retrieved from CAPLUS; Jun. 12, 2009.*
Chen, D., "Synthesis and antibacterial activity of 1,2,4-oxadiazole derivatives" 2010, Huaxue Yanjiu Yu Yingyong, 22 (2), 176-181. Abstract Only.
Guven, O.O., "Synthesis and Characterization of Some Novell 4-furyl substituted 3-imidazoline 3-oxides," 2007, Arkivoc, (XV) 142-147.
Ma, S., "Carbon-13 NMR studies of 3-aryl-4-(5-aryl-Δ2-1,2,4-oxadiazolin-3-yl)sydnones and 3-aryl-4-(5-aryl-1,2,4-oxadiazol-3-yl)sydnones," 1991, Journal of the Chinese Chemical Society, Taipei, Taiwan, 38(3), 247-56.
Poesche, W.H., "1,2,3-Benzothiadiazolium salts. I. The structure of Jacobson's benzothiadiazolium salts," 1964, Journal of the Chemical Society, 5426-30.
Sherman, W.R., et al., "Syntheses with 5-nitro-2-furonitrile," 1965, J Med Chem, 8(1):25-28.
Yeh, M.Y., Preparation of 3-aryl-4-(5-aryl-Δ2-1,2,4-oxadiazolin-3-yl)sydnones and their conversion into 3-aryl-4-(5-aryl-1,2,4-oxadiazol-3-yl)sydnones, 1986, Journal of the Chinese Chemical Society, Taipei, Taiwan, 33(1)/ 61-71.
International Search Report and Written Opinion issued in PCT/US2014/16387 on May 16, 2014, 12 pages.

* cited by examiner

*Primary Examiner* — Shawquia Jackson
(74) *Attorney, Agent, or Firm* — Senniger Powers LLP; Molly B. Edwards

(57) ABSTRACT

Provided herein are new 3,5-disubstituted-4,5-dihydro-1,2,4-oxadiazoles that exhibit nematicidal activity and are useful, for example, in compositions and methods for the control of unwanted nematodes.

54 Claims, No Drawings

3,5-DISUBSTITUTED-4,5-DIHYDRO-1,2,4-OXADIAZOLES AND COMPOSITIONS AND METHODS FOR CONTROLLING NEMATODE PESTS

REFERENCE TO RELATED APPLICATIONS

This application claims the benefit of U.S. Provisional Application Ser. No. 61/788,020, filed Mar. 15, 2013, and U.S. Provisional Application Ser. No. 61/765,477, filed Feb. 15, 2013. The entire contents of both applications are incorporated herein by reference.

FIELD

Provided herein are new 3,5-disubstituted-4,5-dihydro-1,2,4-oxadiazoles that exhibit nematicidal activity and are useful, for example, in compositions and methods for the control of unwanted nematodes.

BACKGROUND

Nematodes are active, flexible, elongate organisms that live on moist surfaces or in liquid environments, including films of water within soil and moist tissues within other organisms. Many species of nematodes have evolved to be very successful parasites of plants and animals and, as a result, are responsible for significant economic losses in agriculture and livestock.

Plant parasitic nematodes can infest all parts of the plant, including the roots, developing flower buds, leaves, and stems. Plant parasites can be classified on the basis of their feeding habits into a few broad categories: migratory ectoparasites, migratory endoparasites, and sedentary endoparasites. Sedentary endoparasites, which include root knot nematodes (*Meloidogyne*) and cyst nematodes (*Globodera* and *Heterodera*), can establish long-term infections within roots that may be very damaging to crops.

There is an urgent need in the industry for effective, economical, and environmentally safe compounds, compositions and methods for controlling nematodes.

SUMMARY

The present disclosure is generally related to a 3,5-disubstituted-4,5-dihydro-1,2,4-oxadiazole of Formula I or a salt thereof,

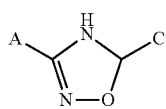

Formula I wherein A is selected from the group consisting of phenyl, pyridyl, pyrazyl, oxazolyl and isoxazolyl, each of which can be optionally independently substituted with one or more substituents selected from the group consisting of halogen, $CF_3$, $CH_3$, $OCF_3$, $OCH_3$, CN, and C(H)O; and C is selected from the group consisting of thienyl, furanyl, oxazolyl, isoxazolyl, pyrrolyl, and pyrrolidinyl, each of which can be optionally independently substituted with one or more substituents selected from the group consisting of alkyl, alkoxy, cycloalkyl, haloalkyl, haloalkoxy, heterocyclyl, and halogen.

In another aspect, the present disclosure is generally related to a 3,5-disubstituted-4,5-dihydro-1,2,4-oxadiazole of Formula II or a salt thereof,

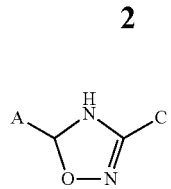

Formula II wherein A is selected from the group consisting of phenyl, pyridyl, pyrazyl, oxazolyl and isoxazolyl, each of which can be optionally independently substituted with one or more substituents selected from the group consisting of halogen, $CF_3$, $CH_3$, $OCF_3$, $OCH_3$, CN, and C(H)O; and C is selected from the group consisting of thienyl, furanyl, oxazolyl, isoxazolyl, pyrrolyl, and pyrrolidinyl, each of which can be optionally independently substituted with one or more with substituents selected from the group consisting of alkyl, alkoxy, cycloalkyl, haloalkyl, haloalkoxy, heterocyclyl, and halogen.

Another aspect of the present disclosure is generally related to a compound selected from the group consisting of: 3-phenyl-5-(thiophen-2-yl)-4,5-dihydro-1,2,4-oxadiazole, or a salt thereof; 5-(furan-2-yl)-3-phenyl-4,5-dihydro-1,2,4-oxadiazole, or a salt thereof; 3-(4-chlorophenyl)-5-(furan-2-yl)-4,5-dihydro-1,2,4-oxadiazole, or a salt thereof; 3-(4-chloro-2-methylphenyl)-5-(furan-2-yl)-4,5-dihydro-1,2,4-oxadiazole, or a salt thereof; 3-(4-fluorophenyl)-5-(thiophen-2-yl)-4,5-dihydro-1,2,4-oxadiazole, or a salt thereof; 3-(4-chlorophenyl)-5-(thiophen-2-yl)-4,5-dihydro-1,2,4-oxadiazole, or a salt thereof; 3-(4-bromophenyl)-5-(thiophen-2-yl)-4,5-dihydro-1,2,4-oxadiazole, or a salt thereof; 3-(4-bromophenyl)-5-(furan-2-yl)-4,5-dihydro-1,2,4-oxadiazole, or a salt thereof; 3-(2,4-dichlorophenyl)-5-(furan-2-yl)-4,5-dihydro-1,2,4-oxadiazole, or a salt thereof; 3-(4-bromophenyl)-5-(furan-3-yl)-4,5-dihydro-1,2,4-oxadiazole, or a salt thereof; 3-(2,4-difluorophenyl)-5-(thiophen-3-yl)-4,5-dihydro-1,2,4-oxadiazole, or a salt thereof; 3-(4-chlorophenyl)-5-(thiophen-3-yl)-4,5-dihydro-1,2,4-oxadiazole, or a salt thereof; 3-(4-chlorophenyl)-5-(furan-3-yl)-4,5-dihydro-1,2,4-oxadiazole, or a salt thereof; 3-(4-fluorophenyl)-5-(thiophen-3-yl)-4,5-dihydro-1,2,4-oxadiazole, or a salt thereof; 3-(4-fluorophenyl)-5-(furan-3-yl)-4,5-dihydro-1,2,4-oxadiazole, or a salt thereof; 3-(4-fluorophenyl)-5-(furan-3-yl)-4,5-dihydro-1,2,4-oxadiazole, or a salt thereof; 5-phenyl-3-(1H-pyrrol-1-yl)-4,5-dihydro-1,2,4-oxadiazole, or a salt thereof; 3-(thiophen-2-yl)-5-(p-tolyl)-4,5-dihydro-1,2,4-oxadiazole, or a salt thereof; 5-(3-chlorophenyl)-3-(thiophen-2-yl)-4,5-dihydro-1,2,4-oxadiazole, or a salt thereof; 5-(4-chloro-2-methylphenyl)-3-(furan-2-yl)-4,5-dihydro-1,2,4-oxadiazole, or a salt thereof; 5-phenyl-3-(thiophen-3-yl)-4,5-dihydro-1,2,4-oxadiazole, or a salt thereof; and 3-phenyl-5-(1H-pyrrol-1-yl)-4,5-dihydro-1,2,4-oxadiazole, or a salt thereof.

Another aspect of the present disclosure is generally related to an aqueous nematicidal composition comprising a 3,5-disubstituted-4,5-dihydro-1,2,4-oxadiazole as described herein.

Another aspect of the present disclosure is generally related to a seed comprising a coating comprising a 3,5-disubstituted-4,5-dihydro-1,2,4-oxadiazole or nematicidal composition as described herein.

Another aspect of the present disclosure is generally related to a method of controlling unwanted nematodes, the method comprising administering to mammals, birds, or their food, plants, seeds, or soil a composition comprising an effective amount of a 3,5-disubstituted-4,5-dihydro-1,2,4-oxadiazole as described herein.

Other objects and features will be in part apparent and in part pointed out hereinafter.

DETAILED DESCRIPTION

Described herein are new 3,5-disubstituted-4,5-dihydro-1,2,4-oxadiazoles that exhibit nematicidal activity. The nematicidal compounds described herein may be used in the preparation of nematicidal compositions and in accordance with methods for control of unwanted nematodes, as set forth in detail below.

For example, in one embodiment, the compound is a 3,5-disubstituted-4,5-dihydro-1,2,4-oxadiazole of Formula I or a salt thereof,

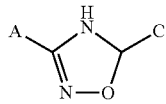

Formula I wherein A is selected from the group consisting of phenyl, pyridyl, pyrazyl, oxazolyl and isoxazolyl, each of which can be optionally independently substituted with one or more substituents selected from the group consisting of halogen, $CF_3$, $CH_3$, $OCF_3$, $OCH_3$, CN, and C(H)O; and C is selected from the group consisting of thienyl, furanyl, oxazolyl, isoxazolyl, pyrrolyl, and pyrrolidinyl, each of which can be optionally independently substituted with one or more substituents selected from the group consisting of alkyl, alkoxy, cycloalkyl, haloalkyl, haloalkoxy, heterocyclyl, and halogen.

In one embodiment, A is phenyl, which may be optionally independently substituted with one or more substituents as described above, and C is thienyl, furanyl, or pyrrolyl, each of which can be optionally independently substituted as described above.

In some embodiments, C is optionally independently substituted with one or more substituents selected from the group consisting of F, Cl, $CH_3$, $CF_3$, Br, $OCH_3$, and $OCF_3$. For example, in one embodiment, C is optionally independently substituted with one or more substituents selected from the group consisting of F, Cl, $CH_3$, and $OCF_3$.

For example, the compound may be a compound of Formula Ia or a salt thereof,

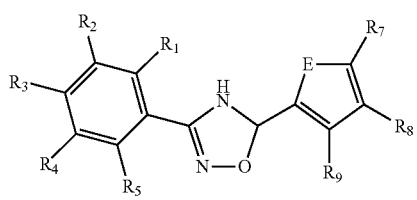

Formula Ia wherein $R_1$ and $R_5$ are independently selected from the group consisting of hydrogen, $CH_3$, F, Cl, Br, $CF_3$ and $OCF_3$; $R_2$ and $R_4$ are independently selected from the group consisting of hydrogen, F, Cl, Br, and $CF_3$; $R_3$ is selected from the group consisting of hydrogen, $CH_3$, $CF_3$, F, Cl, Br, $OCF_3$, $OCH_3$, CN, and C(H)O; $R_7$, $R_8$ and $R_9$ are selected from the group consisting of hydrogen, alkyl, alkoxy, cycloalkyl, haloalkyl, haloalkoxy, heterocyclyl, and halogen; and E is selected from the group consisting of O, S, and N—$R_{10}$, wherein $R_{10}$ is alkyl.

In some embodiments, $R_7$, $R_8$, and $R_9$ are independently selected from the group consisting of hydrogen, F, Cl, $CH_3$, and $OCF_3$. For example, in one embodiment, $R_7$ and $R_8$ are independently selected from the group consisting of hydrogen and F; and $R_9$ is selected from the group consisting of hydrogen, F, Cl, $CH_3$, and $OCF_3$.

Alternatively, the compound may be a compound of Formula Ib or a salt thereof,

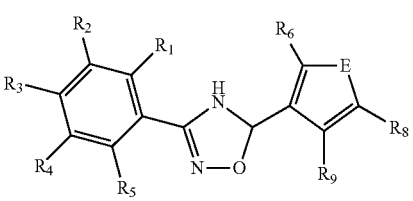

Formula Ib wherein $R_1$ and $R_5$ are independently selected from the group consisting of hydrogen, $CH_3$, F, Cl, Br, $CF_3$ and $OCF_3$; $R_2$ and $R_4$ are independently selected from the group consisting of hydrogen, F, Cl, Br, and $CF_3$; $R_3$ is selected from the group consisting of hydrogen, $CH_3$, $CF_3$, F, Cl, Br, $OCF_3$, $OCH_3$, CN, and C(H)O; $R_6$, $R_8$ and $R_9$ are selected from the group consisting of hydrogen, alkyl, alkoxy, cycloalkyl, haloalkyl, haloalkoxy, heterocyclyl, and halogen; and E is selected from the group consisting of O, S, and N—$R_{10}$, wherein $R_{10}$ is alkyl.

In some embodiments, $R_6$, $R_8$, and $R_9$ are independently selected from the group consisting of hydrogen, F, Cl, $CH_3$, and $OCF_3$. For example, in one embodiment, $R_8$ is selected from hydrogen and F; and $R_6$ and $R_9$ are independently selected from the group consisting of hydrogen, F, Cl, $CH_3$, and $OCF_3$.

Alternatively, the compound may be a compound of Formula Ic or a salt thereof,

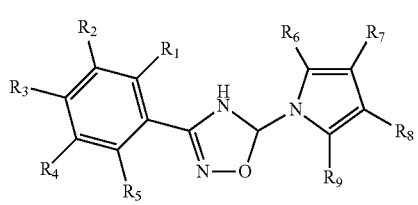

Formula Ic wherein $R_1$ and $R_5$ are independently selected from the group consisting of hydrogen, $CH_3$, F, Cl, Br, $CF_3$ and $OCF_3$; $R_2$ and $R_4$ are independently selected from the group consisting of hydrogen, F, Cl, Br and $CF_3$; $R_3$ is selected from the group consisting of hydrogen, $CH_3$, $CF_3$, F, Cl, Br, $OCF_3$, $OCH_3$, CN, and C(H)O; and $R_6$, $R_7$, $R_8$ and $R_9$ are selected from the group consisting of hydrogen, alkyl, alkoxy, cycloalkyl, haloalkyl, haloalkoxy, heterocyclyl, and halogen.

In some embodiments, $R_6$, $R_7$, $R_8$, and $R_9$ are independently selected from the group consisting of hydrogen, $CH_3$, $CF_3$, F, Cl, Br, $OCF_3$, and $OCH_3$.

In another embodiment, the compound is a 3,5-disubstituted-4,5-dihydro-1,2,4-oxadiazole of Formula II or a salt thereof, Formula II

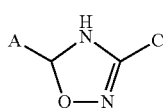

wherein A is selected from the group consisting of phenyl, pyridyl, pyrazyl, oxazolyl and isoxazolyl, each of which can be optionally independently substituted with one or more substituents selected from the group consisting of halogen, $CF_3$, $CH_3$, $OCF_3$, $OCH_3$, CN, and C(H)O; and C is selected from the group consisting of thienyl, furanyl, oxazolyl, isoxazolyl, pyrrolyl, and pyrrolidinyl, each of which can be optionally independently substituted with one or more substituents selected from the group consisting of alkyl, alkoxy, cycloalkyl, haloalkyl, haloalkoxy, heterocyclyl, and halogen.

In one embodiment, A is phenyl, which may be optionally independently substituted with one or more substituents as described above, and C is thienyl, furanyl, or pyrrolyl, each of which can be optionally independently substituted as described above.

In some embodiments, C is optionally independently substituted with one or more substituents selected from the group consisting of F, Cl, $CH_3$, $CF_3$, Br, $OCH_3$, and $OCF_3$. For example, in one embodiment, C is optionally independently substituted with one or more substituents selected from the group consisting of F, Cl, $CH_3$, and $OCF_3$.

For example, the compound may be a compound of Formula IIa or a salt thereof,

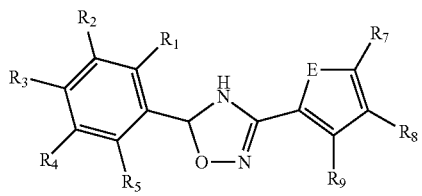

Formula IIa wherein $R_1$ and $R_5$ are independently selected from the group consisting of hydrogen, $CH_3$, F, Cl, Br, $CF_3$ and $OCF_3$; $R_2$ and $R_4$ are independently selected from the group consisting of hydrogen, F, Cl, Br, and $CF_3$; $R_3$ is selected from the group consisting of hydrogen, $CH_3$, $CF_3$, F, Cl, Br, $OCF_3$, $OCH_3$, CN, and C(H)O; $R_7$, $R_8$ and $R_9$ are selected from the group consisting of hydrogen, alkyl, alkoxy, cycloalkyl, haloalkyl, haloalkoxy, heterocyclyl, and halogen; and E is selected from the group O, S, and N—$R_{10}$, wherein $R_{10}$ is alkyl.

In some embodiments, $R_7$, $R_8$, and $R_9$ are independently selected from the group consisting of hydrogen, F, Cl, $CH_3$, and $OCF_3$. For example, in one embodiment, $R_7$ and $R_8$ are independently selected from the group consisting of hydrogen and F; and $R_9$ is selected from the group consisting of hydrogen, F, Cl, $CH_3$, and $OCF_3$.

Alternatively, the compound may be a compound of Formula IIb or a salt thereof,

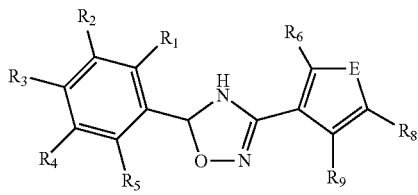

Formula IIb wherein $R_1$ and $R_5$ are independently selected from the group consisting of hydrogen, $CH_3$, F, Cl, Br, $CF_3$ and $OCF_3$; $R_2$ and $R_4$ are independently selected from the group consisting of hydrogen, F, Cl, Br, and $CF_3$; $R_3$ is selected from the group consisting of hydrogen, $CH_3$, $CF_3$, F, Cl, Br, $OCF_3$, $OCH_3$, CN, and C(H)O; $R_6$, $R_8$ and $R_9$ are selected from the group consisting of hydrogen, alkyl, alkoxy, cycloalkyl, haloalkyl, haloalkoxy, heterocyclyl, and halogen; and E is selected from the group O, S, and N—$R_{10}$, wherein $R_{10}$ is alkyl.

In some embodiments, $R_6$, $R_8$, and $R_9$ are independently selected from the group consisting of hydrogen, F, Cl, $CH_3$, and $OCF_3$. For example, in one embodiment, $R_8$ is selected from the group consisting of hydrogen and F; and $R_6$ and $R_9$ are independently selected from the group consisting of hydrogen, F, Cl, $CH_3$, and $OCF_3$.

Alternatively, the compound may be a compound of Formula IIc or a salt thereof,

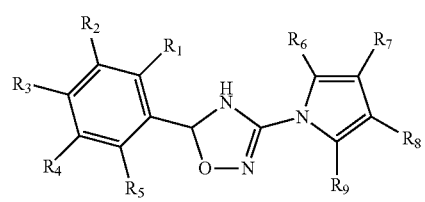

Formula IIc wherein $R_1$ and $R_5$ are independently selected from the group consisting of hydrogen, $CH_3$, F, Cl, Br, $CF_3$ and $OCF_3$; $R_2$ and $R_4$ are independently selected from the group consisting of hydrogen, F, Cl, Br and $CF_3$; $R_3$ is selected from the group consisting of hydrogen, $CH_3$, $CF_3$, F, Cl, Br, $OCF_3$, $OCH_3$, CN, and C(H)O; and $R_6$, $R_7$, $R_8$ and $R_9$ are selected from the group consisting of hydrogen, alkyl, alkoxy, cycloalkyl, haloalkyl, haloalkoxy, heterocyclyl, and halogen.

In one embodiment, $R_6$, $R_7$, $R_8$, and $R_9$ are independently selected from the group consisting of hydrogen, F, Cl, $CH_3$, $CF_3$, Br, $OCH_3$, and $OCF_3$.

As used herein, the terms "halo" or "halogen" refer to any radical of fluorine, chlorine, bromine or iodine.

The term "alkyl" as employed herein, by itself or as part of another group, refers to both straight and branched chain radicals of up to ten carbons. Non-limiting examples of $C_1$-$C_{10}$ alkyl groups include methyl, ethyl, propyl, isopropyl, butyl, sec-butyl, tert-butyl, 3-pentyl, hexyl and octyl groups, each of which may be optionally independently substituted.

The term "cycloalkyl" as used herein typically refers to an alkyl group comprising a closed ring comprising from 3 to 8 carbon atoms. Non-limiting examples of cycloalkyl groups include cyclopropyl, cyclobutyl, cyclopentyl, cyclohexyl and cycloheptyl, each of which may be optionally independently substituted.

As used herein, the term "heterocyclyl," or heterocycle, refers to a saturated or partially saturated 3 to 7 membered monocyclic, or 7 to 10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or on a nitrogen atom if the resulting compound is stable. Non-limiting examples of common saturated or partially saturated heterocyclic groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetronoyl and tetramoyl groups.

The term "haloalkyl" as employed herein, by itself or as part of another group, refers to an alkyl group, as defined herein, substituted with at least one halogen. Non-limiting examples of haloalkyl groups include trifluoromethyl, and 2,2,2-trifluoroethyl.

The term "alkoxy" as employed herein, by itself or as part of another group, refers to an alkyl group, as defined herein, appended to the parent molecular moiety through an oxygen atom. Non-limiting examples of alkoxy groups include methoxy, ethoxy, propoxy, 2-propoxy, butoxy, tert-butoxy, pentyloxy, and hexyloxy, each of which may be optionally independently substituted.

The term "haloalkoxy" as employed herein, by itself or as part of another group, refers to an alkoxy group as defined herein, wherein the alkyl moiety of the alkoxy group is further substituted with at least one halogen. Non-limiting examples of haloalkoxy groups include trifluoromethoxy, and 2,2-dichloroethoxy.

In one embodiment, the compound is a compound of Formula Ia or IIa wherein each of $R_7$, $R_8$ and $R_9$ is hydrogen or, similarly, a compound of Formula Ib or IIb wherein each of $R_6$, $R_8$ and $R_9$ is hydrogen or, similarly, a compound of Formula Ic or IIc wherein each of $R_6$, $R_7$, $R_8$ and $R_9$ is hydrogen. In some embodiments, each of $R_1$, $R_2$, $R_3$, $R_4$, and $R_5$ is also hydrogen. In other embodiments, at least one of $R_1$, $R_2$, $R_3$, $R_4$, and $R_5$ is other than hydrogen. For example, in some embodiments, at least one of $R_1$, $R_2$, $R_3$, $R_4$, and $R_5$ is independently selected from the group consisting of halogen and $CH_3$. In some embodiments, at least one of $R_1$, $R_2$, $R_3$, $R_4$, and $R_5$ is halogen.

In one embodiment, the compound is a 3,5-disubstituted-4,5-dihydro-1,2,4-oxadiazole of Formula Ia or a salt thereof. Non-limiting examples of species include 3-phenyl-5-(thiophen-2-yl)-4,5-dihydro-1,2,4-oxadiazole of Formula Ia-i, or a salt thereof,

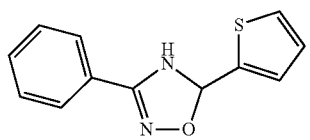

Formula Ia-i 5-(furan-2-yl)-3-phenyl-4,5-dihydro-1,2,4-oxadiazole of formula Ia-ii, or a salt thereof,

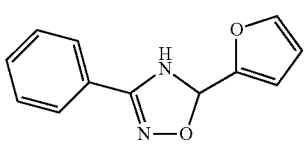

Formula Ia-ii 3-(4-chlorophenyl)-5-(furan-2-yl)-4,5-dihydro-1,2,4-oxadiazole of Formula Ia-iii, or a salt thereof,

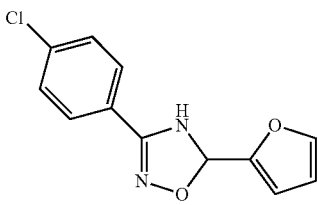

Formula Ia-iii 3-(4-chloro-2-methylphenyl)-5-(furan-2-yl)-4,5-dihydro-1,2,4-oxadiazole of Formula Ia-iv, or a salt thereof,

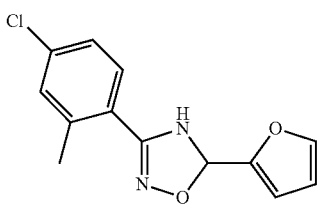

Formula Ia-iv 3-(4-fluorophenyl)-5-(thiophen-2-yl)-4,5-dihydro-1,2,4-oxadiazole of Formula Ia-v, or a salt thereof,

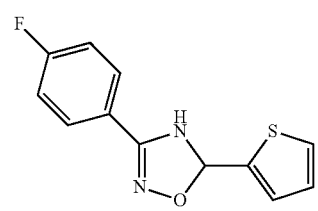

Formula Ia-v 3-(4-chlorophenyl)-5-(thiophen-2-yl)-4,5-dihydro-1,2,4-oxadiazole of Formula Ia-vi, or a salt thereof,

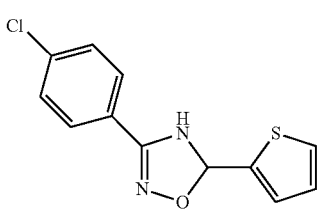

Formula Ia-vi 3-(4-bromophenyl)-5-(thiophen-2-yl)-4,5-dihydro-1,2,4-oxadiazole of Formula Ia-vii, or a salt thereof,

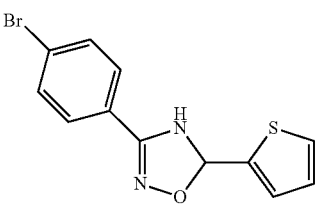

Formula Ia-vii 3-(4-bromophenyl)-5-(furan-2-yl)-4,5-dihydro-1,2,4-oxadiazole of Formula Ia-viii, or a salt thereof,

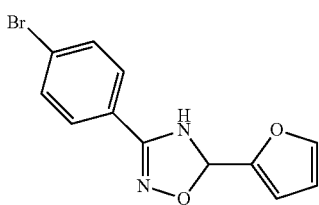

and 3-(2,4-dichlorophenyl)-5-(furan-2-yl)-4,5-dihydro-1,2,4-oxadiazole of Formula Ia-ix, or a salt thereof,

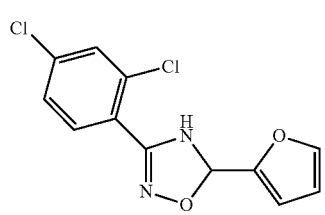

In another embodiment, the compound is a 3,5-disubstituted-4,5-dihydro-1,2,4-oxadiazole of Formula Ib or a salt thereof. Non-limiting examples of species include 3-(4-bromophenyl)-5-(furan-3-yl)-4,5-dihydro-1,2,4-oxadiazole of Formula Ib-i, or a salt thereof,

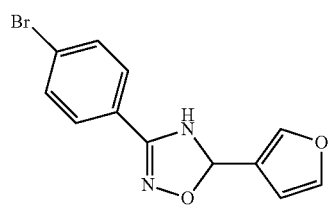

3-(2,4-difluorophenyl)-5-(thiophen-3-yl)-4,5-dihydro-1,2,4-oxadiazole of Formula Ib-ii, or a salt thereof,

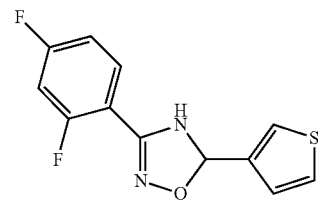

3-(4-chlorophenyl)-5-(thiophen-3-yl)-4,5-dihydro-1,2,4-oxadiazole of Formula Ib-iii, or a salt thereof,

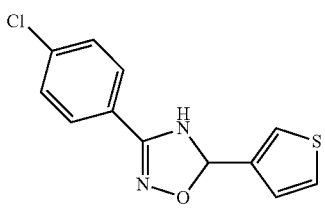

3-(4-chlorophenyl)-5-(furan-3-yl)-4,5-dihydro-1,2,4-oxadiazole of Formula Ib-iv, or a salt thereof,

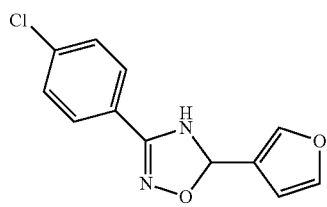

3-(4-fluorophenyl)-5-(thiophen-3-yl)-4,5-dihydro-1,2,4-oxadiazole of Formula Ib-v, or a salt thereof,

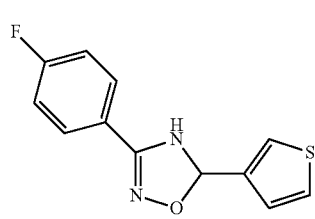

and 3-(4-fluorophenyl)-5-(furan-3-yl)-4,5-dihydro-1,2,4-oxadiazole of Formula Ib-vi, or a salt thereof

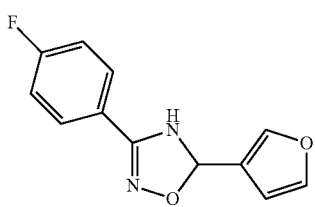

In another embodiment, the compound is a 3,5-disubstituted-4,5-dihydro-1,2,4-oxadiazole of Formula Ic or a salt thereof. A non-limiting example of a species is 3-phenyl-5-(1H-pyrrol-1-yl)-4,5-dihydro-1,2,4-oxadiazole of Formula Ic-i, or a salt thereof

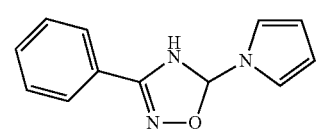

In another embodiment, the compound is a 3,5-disubstituted-4,5-dihydro-1,2,4-oxadiazole of Formula IIa or a salt thereof. Non-limiting examples of species include 3-(thiophen-2-yl)-5-(p-tolyl)-4,5-dihydro-1,2,4-oxadiazole of Formula IIa-i, or a salt thereof,

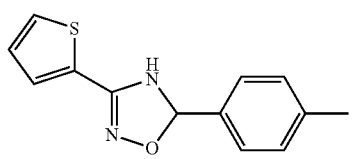

5-(3-chlorophenyl)-3-(thiophen-2-yl)-4,5-dihydro-1,2,4-oxadiazole of Formula IIa-ii, or a salt thereof,

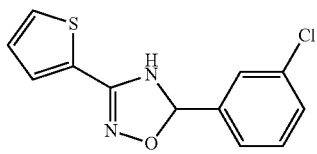

Formula IIa-ii and 5-(4-chloro-2-methylphenyl)-3-(furan-2-yl)-4,5-dihydro-1,2,4-oxadiazole of Formula IIa-iii, or a salt thereof.

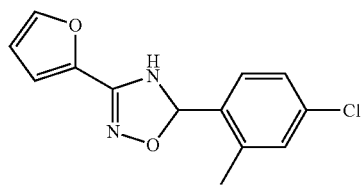

Formula IIa-iii

In another embodiment, the compound is a 3,5-disubstituted-4,5-dihydro-1,2,4-oxadiazole of Formula IIb or a salt thereof. A non-limiting example of a species is 5-phenyl-3-(thiophen-3-yl)-4,5-dihydro-1,2,4-oxadiazole of Formula IIb-i and salts thereof.

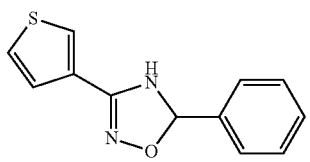

Formula IIb-i

In another embodiment, the compound is a 3,5-disubstituted-4,5-dihydro-1,2,4-oxadiazole of Formula IIc, or a salt thereof. A non-limiting examples of a species is 5-phenyl-3-(1H-pyrrol-1-yl)-4,5-dihydro-1,2,4-oxadiazole of Formula IIc-i, or a salt thereof.

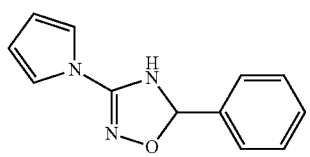

Formula IIc-i

Enantiomers

The compounds described above can be present as a racemic mixture, as a mixture of two enantiomers at different ratios, or as a single enantiomer. Compositions that are enriched with respect to one enantiomer, or which comprise substantially a single enantiomer, may be prepared using chiral separation techniques known in the art (e.g., chiral chromatography or asymmetric synthesis).

Methods of Use

Generally, the nematicidal compounds described herein can be applied to seeds, plants, or the environment of plants needing nematode control, or to animals or the food of animals needing nematode parasite control.

For example, one embodiment of the present disclosure is generally related to a method for control of unwanted nematodes, the method comprising administering to mammals, birds, or their food, plants, seeds or soil a composition comprising an effective amount of a 3,5-disubstituted-4,5-dihydro-1,2,4-oxadiazole as described herein.

Application to Seeds

One aspect of the present disclosure is related to a method of protecting a seed, and/or the roots of a plant grown from the seed, against damage by a nematode. In one embodiment, the method comprises treating a seed with a seed treatment composition comprising a 3,5-disubstituted-4,5-dihydro-1,2,4-oxadiazole as described herein.

The seed treatment methods described herein can be used in connection with any species of plant and/or the seeds thereof. In various embodiments, however, the methods are used in connection with seeds of plant species that are agronomically important, Ire particular, the seeds can be of corn, peanut, canola/rapeseed, soybean, cucurbits, crucifers, cotton, beets, rice, sorghum, sugar beet, wheat, barley, rye, sunflower, tomato, sugarcane, tobacco, oats, as well as other vegetable and leaf crops. In some embodiments, the seed is corn, soybean, or cotton seed. The seed may be a transgenic seed from which a transgenic plant can grow and incorporates a transgenic event that confers, for example, tolerance to a particular herbicide or combination of herbicides, increased disease resistance, enhanced tolerance to stress and/or enhanced yield. Transgenic seeds include, but are not limited to, seeds of corn, soybean and cotton.

The seed treatment method may comprise applying the seed treatment composition to the seed prior to sowing the seed, so that the sowing operation is simplified. In this manner, seeds can be treated, for example, at a central location and then distributed for planting. This permits the person who plants the seeds to avoid the complexity and effort associated with handling and applying the seed treatment compositions, and to merely handle and plant the treated seeds in a manner that is conventional for regular untreated seeds.

The seed treatment composition can be applied to seeds by any standard seed treatment methodology, including but not limited to mixing in a container (e.g., a bottle or bag), mechanical application, tumbling, spraying, immersion, and solid matrix priming. Seed coating methods and apparatus for their application are disclosed in, for example, U.S. Pat. Nos. 5,918,413, 5,891,246, 5,554,445, 5,389,399, 5,107,787, 5,080,925, 4,759,945 and 4,465,017, among others. Any conventional active or inert material can be used for contacting seeds with the seed treatment composition, such as conventional film-coating materials including but not limited to water-based film coating materials.

For example, in one embodiment, a seed treatment composition can be introduced onto or into a seed by use of solid matrix priming. For example, a quantity of the seed treatment composition can be mixed with a solid matrix material and then the seed can be placed into contact with the solid matrix material for a period to allow the seed treatment composition to be introduced to the seed. The seed can then optionally be separated from the solid matrix material and stored or used, or the mixture of solid matrix material plus seed can be stored or planted directly. Solid matrix materials which are useful include polyacrylamide, starch, clay, silica, alumina, soil, sand, polyurea, polyacrylate, or any other material capable of absorbing or adsorbing the seed treatment composition for a time and releasing the nematicide of the seed treatment composition into or onto the seed. It is useful to make sure that the nematicide and the solid matrix material are compatible with each other. For example, the solid matrix material should be chosen so that it can release the nematicide at a reasonable rate, for example over a period of minutes, hours, days, or weeks.

Imbibition is another method of treating seed with the seed treatment composition. For example, a plant seed can be directly immersed for a period of time in the seed treatment composition. During the period that the seed is immersed, the seed takes up, or imbibes, a portion of the seed treatment composition. Optionally, the mixture of plant seed and the seed treatment composition can be agitated, for example by shaking, rolling, tumbling, or other means. After imbibition, the seed can be separated from the seed treatment composition and optionally dried, for example by patting or air drying.

The seed treatment composition may be applied to the seeds using conventional coating techniques and machines, such as fluidized bed techniques, the roller mill method, rotostatic seed treaters, and drum coaters. Other methods, such as spouted beds may also be useful. The seeds may be pre-sized before coating. After coating, the seeds are typically dried and then transferred to a sizing machine for sizing. Such procedures are generally known in the art.

If the seed treatment composition is applied to the seed in the form of a coating, the seeds can be coated using a variety of methods known in the art. For example, the coating process can comprise spraying the seed treatment composition onto the seed while agitating the seed in an appropriate piece of equipment such as a tumbler or a pan granulator.

In one embodiment, when coating seed on a large scale (for example a commercial scale), the seed coating may be applied using a continuous process. Seed may be introduced into the treatment equipment (such as a tumbler, a mixer, or a pan granulator) either by weight or by flow rate. The amount of treatment composition that is introduced into the treatment equipment can vary depending on the seed weight to be coated, surface area of the seed, the concentration of the nematicide and/or other active ingredients in the treatment composition, the desired concentration on the finished seed, and the like. The treatment composition can be applied to the seed by a variety of means, for example by a spray nozzle or revolving disc. The amount of liquid may be determined by the assay of the formulation and the required rate of active ingredient necessary for efficacy. As the seed falls into the treatment equipment the seed can be treated (for example by misting or spraying with the seed treatment composition) and passed through the treater under continual movement/tumbling where it can be coated evenly and dried before storage or use.

In another embodiment, the seed coating may be applied using a batch process. For example, a known weight of seeds can be introduced into the treatment equipment (such as a tumbler, a mixer, or a pan granulator). A known volume of seed treatment composition can be introduced into the treatment equipment at a rate that allows the seed treatment composition to be applied evenly over the seeds. During the application, the seed can be mixed, for example by spinning or tumbling. The seed can optionally be dried or partially dried during the tumbling operation. After complete coating, the treated sample can be removed to an area for further drying or additional processing, use, or storage.

In an alternative embodiment, the seed coating may be applied using a semi-batch process that incorporates features from each of the batch process and continuous process embodiments set forth above.

In still another embodiment, seeds can be coated in laboratory size commercial treatment equipment such as a tumbler, a mixer, or a pan granulator by introducing a known weight of seeds in the treater, adding the desired amount of seed treatment composition, tumbling or spinning the seed and placing it on a tray to thoroughly dry.

In another embodiment, seeds can also be coated by placing the known amount of seed into a narrow neck bottle or receptacle with a lid. While tumbling, the desired amount of seed treatment composition can be added to the receptacle. The seed is tumbled until it is coated with the treatment composition. After coating, the seed can optionally be dried, for example on a tray.

In some embodiments, the treated seeds may also be enveloped with a film overcoating to protect the nematicidal coating. Such overcoatings are known in the art and may be applied using conventional fluidized bed and drum film coating techniques. The overcoatings may be applied to seeds that have been treated with any of the seed treatment techniques described above, including but not limited to solid matrix priming, imbibition, coating, and spraying, or by any other seed treatment technique known in the art.

Application to Plants and/or Soil

Another embodiment of the present disclosure is generally related to protecting a plant against damage by a nematode. For example, in one embodiment, a treatment composition comprising a 3,5-disubstituted-4,5-dihydro-1,2,4-oxadiazole as described herein may be supplied to a plant exogenously. The treatment composition may be applied to the plant and/or the surrounding soil through sprays, drips, and/or other forms of liquid application. In one embodiment, a treatment composition comprising the nematicidal compound is directly applied to the soil surrounding the root zone of a plant. Soil applications may require 0.5 to 2 kg per hectare on a broadcast basis (rate per treated area if broadcast or banded).

The application may be performed using any method or apparatus known in the art, including but not limited to hand sprayer, mechanical sprinkler, or irrigation, including drip irrigation.

For example, in one embodiment, the nematicidal treatment composition is applied to plants and/or soil using a drip irrigation technique. In one embodiment, the nematicidal treatment composition is applied directly to the base of the plants or the soil immediately adjacent to the plants. The composition may be applied through existing drip irrigation systems. This procedure is particularly preferred for use in connection with cotton, strawberries, tomatoes, potatoes, vegetables, and ornamental plants.

In another embodiment, the nematicidal treatment composition is applied to plants and/or soil using a drench application. Preferably, a sufficient quantity of the nematicidal treatment composition is applied such that it drains through the soil to the root area of the plants. The drench application technique may be preferred for use in connection with crop plants, turf grasses, and animals.

In some embodiments, the nematicidal composition is applied to soil after planting. In other embodiments, however, the nematicidal composition may be applied to soil during planting. In other embodiments, however, the nematicidal composition may be applied to soil before planting. When the nematicidal composition is applied directly to the soil, it may be applied using any method known in the art. For example, it may be tilled into the soil or applied in furrow.

Administration to Animals

Another embodiment of the present disclosure is generally related to a method of controlling unwanted nematodes, the method comprising administering to an animal a nematicidal treatment composition comprising a 3,5-disubstituted-4,5-dihydro-1,2,4-oxadiazole as described herein. For example, in one embodiment, the nematicidal treatment composition may be administered to an animal orally to promote activity against internal parasitic nematodes. In another embodiment, the nematicidal treatment composition may be administered by injection of the host animal. In another embodiment, the nematicidal treatment composition may be administered to the host animal by topical application.

In some embodiments, the nematicidal composition is formulated for topical applications such as pour-ons, or for the use in tags or collars. In these embodiments, it is particularly preferred that the host animal is a non-human animal.

The nematicidal compositions described herein can be applied to any vertebrate animal (e.g., a bird or a mammal). The bird can be a domesticated fowl (e.g., a chicken, turkey, duck, or goose). The mammal can be a domesticated animal, e.g., a companion animal (e.g., a cat, dog, horse or rabbit) or livestock (e.g., a cow, sheep, pig, goat, alpaca or llama). Alternatively, the mammal can be a human.

Another embodiment of the present disclosure is generally related to a nematicidal feed for a non-human vertebrate, wherein the nematicidal feed comprises (a) a feed; and (b) a nematicidal composition comprising a 3,5-disubstituted-4,5-dihydro-1,2,4-oxadiazole as described herein. In some embodiments, the feed is selected from the group consisting of: soy, wheat, corn, sorghum, millet, alfalfa, clover, and rye. Another embodiment is directed to a method of supplementing an animal feed to include one or more of the nematicidal compounds described herein.

Treated Seeds

Another embodiment of the present disclosure is generally related to a seed that has been treated with a seed treatment composition comprising a 3,5-disubstituted-4,5-dihydro-1,2,4-oxadiazole as described herein. Typically, the seed has been treated with the seed treatment composition using one of the seed treatment methods set forth above, including but not limited to solid matrix priming, imbibition, coating, and spraying. For example, the seed may comprise a coating comprising a 3,5-disubstituted-4,5-dihydro-1,2,4-oxadiazole as described herein. The seed may be of any plant species, as described above. The treated seeds comprise the nematicidal compound in an amount of at least about 0.1 mg/seed, in one embodiment from about 0.1 to about 1 mg/seed, and in another embodiment from about 0.1 to about 0.5 mg/seed.

Nematicidal Compositions

The 4,5-dihydro-1,2,4-oxadiaozle compounds described herein offer a number of favorable physiochemical properties with respect to agrochemical products, including favorable aqueous solubility and lipophilicity. Accordingly, in one embodiment, the present disclosure is generally related to a nematicidal composition comprising an effective amount of a 3,5-disubstituted-4,5-dihydro-1,2,4-oxadiazole as described herein. The nematicidal composition may be an aqueous composition.

Generally, the nematicidal compositions described herein can comprise any adjuvants, excipients, or other desirable components known in the art. For example, in some embodiments, the nematicidal composition further comprises a surfactant.

Examples of anionic surfactants include alkyl sulfates, alcohol sulfates, alcohol ether sulfates, alpha olefin sulfonates, alkylaryl ether sulfates, arylsulfonates, alkylsulfonates, alkylaryl sulfonates, sulfosuccinates, mono- or diphosphate esters of polyalkoxylated alkyl alcohols or alkyl phenols, mono- or disulfosuccinate esters of alcohols or polyalkoxylated alkanols, alcohol ether carboxylates, phenol ether carboxylates. In one embodiment, the surfactant is an alkylaryl sulfonate.

Non-limiting examples of commercially available anionic surfactants include sodium dodecylsulfate (Na-DS, SDS), MORWET D-425 (a sodium salt of alkyl naphthalene sulfonate condensate, available from Akzo Nobel), MORWET D-500 (a sodium salt of alkyl naphthalene sulfonate condensate with a block copolymer, available from Akzo Nobel), sodium dodecylbenzene sulfonic acid (Na-DBSA) (available from Aldrich), diphenyloxide disulfonate, naphthalene formaldehyde condensate, DOWFAX (available from Dow), dihexylsulfosuccinate, and dioctylsulfosuccinate, alkyl naphthalene sulfonate condensates, and salts thereof.

Examples of non-ionic surfactants include sorbitan esters, ethoxylated sorbitan esters, alkoxylated alkylphenols, alkoxylated alcohols, block copolymer ethers, and lanolin derivatives. In accordance with one embodiment, the surfactant comprises an alkylether block copolymer.

Non-limiting examples of commercially available non-ionic surfactants include SPAN 20, SPAN 40, SPAN 80, SPAN 65, and SPAN 85 (available from Aldrich); TWEEN 20, TWEEN 40, TWEEN 60, TWEEN 80, and TWEEN 85 (available from Aldrich); IGEPAL CA-210, IGEPAL CA-520, IGEPAL CA-720, IGEPAL CO-210, IGEPAL CO-520, IGEPAL CO-630, IGEPAL CO-720, IGEPAL CO-890, and IGEPAL DM-970 (available from Aldrich); Triton X-100 (available from Aldrich); BRIJ S10, BRIJ S20, BRIJ 30, BRIJ 52, BRIJ 56, BRIJ 58, BRIJ 72, BRIJ 76, BRIJ 78, BRIJ 92V, BRIJ 97, and BRIJ 98 (available from Aldrich); PLURONIC L-31, PLURONIC L-35, PLURONIC L-61, PLURONIC L-81, PLURONIC L-64, PLURONIC L-121, PLURONIC 10R5, PLURONIC 17R4, and PLURONIC 31R1 (available from Aldrich); Atlas G-5000 and Atlas G-5002L (available from Croda); ATLOX 4912 and ATLOX 4912-SF (available from Croda); and SOLUPLUS (available from BASF), LANEXOL AWS (available from Croda).

Non-limiting examples of cationic surfactants include mono alkyl quaternary amine, fatty acid amide surfactants, amidoamine, imidazoline, and polymeric cationic surfactants.

In some embodiments, the nematicidal composition comprises a co-solvent. in addition to water. Non-limiting examples of co-solvents that can be used include, ethyl lactate, methyl soyate/ethyl lactate co-solvent blends (e.g., STEPOSOL, available from Stepan), isopropanol, acetone, 1,2-propanediol, n-alkylpyrrolidones (e.g., the AGSOLEX series, available from ISP), a petroleum based-oil (e.g., AROMATIC series and SOLVESSO series available from Exxon Mobil), isoparaffinic fluids (e.g. ISOPAR series, available from Exxon Mobil), cycloparaffinic fluids (e.g. NAPPAR 6, available from Exxon Mobil), mineral spirits (e.g. VARSOL series available from Exxon Mobil), and mineral oils (e.g., paraffin oil).

Particular examples of commercially available organic solvents include pentadecane, ISOPAR M, ISOPAR V, and ISOPAR L (available from Exxon Mobil).

In some embodiments, the nematicidal composition may be formulated, mixed in a seed treater tank or combined on the seed by overcoating with one or more additional active ingredients. The additional active ingredient may be, for example, an insecticide, a fungicide, an herbicide, or an additional nematicide.

Non-limiting examples of insecticides and nematicides include carbamates, diamides, macrocyclic lactones, neonicotinoids, organophosphates, phenylpyrazoles, pyrethrins, spinosyns, synthetic pyrethroids, tetronic and tetramic acids. In particular embodiments insecticides and nematicides include abamectin, aldicarb, aldoxycarb, bifenthrin, carbofuran, chlorantraniliprole, clothianidin, cyfluthrin, cyhalothrin, cypermethrin, deltamethrin, dinotefuran, emamectin, ethiprole, fenamiphos, fipronil, flubendiamide, fosthiazate, imidacloprid, ivermectin, lambda-cyhalothrin, milbemectin, nitenpyram, oxamyl, permethrin, spinetoram, spinosad, spirodichlofen, spirotetramat, tefluthrin, thiacloprid, thiamethoxam, and thiodicarb.

Non-limiting examples of useful fungicides include aromatic hydrocarbons, benzimidazoles, benzthiadiazole, carboxamides, carboxylic acid amides, morpholines, phenylamides, phosphonates, quinone outside inhibitors (e.g. strobilurins), thiazolidines, thiophanates, thiophene carboxamides, and triazoles. Particular examples of fungicides include acibenzolar-5-methyl, azoxystrobin, benalaxyl, bixafen, boscalid, carbendazim, cyproconazole, dimethomorph, epoxiconazole, fluopyram, fluoxastrobin, flutianil, flutolanil, fluxapyroxad, fosetyl-Al, ipconazole, isopyrazam, kresoximmethyl, mefenoxam, metalaxyl, metconazole, myclobutanil, orysastrobin, penflufen, penthiopyrad, picoxystrobin, propiconazole, prothioconazole, pyraclostrobin, sedaxane, silthiofam, tebuconazole, thifluzamide, thiophanate, tolclofos-methyl, trifloxystrobin, and triticonazole.

Non-limiting examples of herbicides include ACCase inhibitors, acetanilides, AHAS inhibitors, carotenoid biosynthesis inhibitors, EPSPS inhibitors, glutamine synthetase inhibitors, PPO inhibitors, PS II inhibitors, and synthetic auxins, Particular examples of herbicides include acetochlor, clethodim, dicamba, flumioxazin, fomesafen, glyphosate, glufosinate, mesotrione, quizalofop, saflufenacil, sulcotrione, and 2,4-D.

Additional actives may also comprise substances such as, biological control agents, microbial extracts, plant growth activators or plant defense agents. Non-limiting examples of biological control agents include bacteria, fungi, beneficial nematodes, and viruses.

In certain embodiments, the biological control agent can be a bacterium of the genus *Actinomycetes, Agrobacterium, Arthrobacter, Alcaligenes, Aureobacterium, Azobacter, Beijerinckia, Brevibacillus, Burkholderia, Chromobacterium, Clostridium, Clavibacter, Comomonas, Corynebacterium, Curtobacterium, Enterobacter, Flavobacterium, Gluconobacter, Hydrogenophaga, Klebsiella, Methylobacterium, Paenibacillus, Pasteuria, Phingobacterium, Photorhabdus, Phyllobacterium, Pseudomonas, Rhizobium, Serratia, Stenotrophomonas, Variovorax,* and *Xenorhabdus*. In particular embodiments the bacteria is selected from the group consisting of *Bacillus amyloliquefaciens, Bacillus cereus, Bacillus firmus, Bacillus, lichenformis, Bacillus pumilus, Bacillus sphaericus, Bacillus subtilis, Bacillus thuringiensis, Chromobacterium suttsuga, Pasteuria penetrans, Pasteuria usage,* and *Pseudomona fluorescens*.

In certain embodiments the biological control agent can be a fungus of the genus *Alternaria, Ampelomyces, Aspergillus, Aureobasidium, Beauveria, Colletotrichum, Coniothyrium, Gliocladium, Metarhisium, Muscodor, Paecilonyces, Trichoderma, Typhula, Ulocladium,* and *Verticilium*. In particular embodiments the fungus is *Beauveria bassiana, Coniothyrium minitans, Gliocladium vixens, Muscodor albus, Paecilomyces lilacinus,* or *Trichoderma polysporum*.

In further embodiments the biological control agents can be plant growth activators or plant defense agents including, but not limited to harpin, *Reynoutria sachalinensis*, jasmonate, lipochitooligosaccharides, and isoflavones.

The nematicidal compositions described herein exhibit measurable nematode-killing activity or results in reduced fertility or sterility in the nematodes such that fewer viable or no offspring result, or compromise the ability of the nematode to infect or reproduce in its host, or interfere with the growth or development of a nematode. The nematicidal composition may also display nematode repellant properties.

For example, the nematicidal compositions described herein may reduce the survival time of adult nematodes relative to unexposed similarly staged adults, e.g., by about 20%, 40%, 60%, 80%, or more. In some embodiments, the nematicidal compositions described herein may cause the nematodes to cease replicating, regenerating, and/or producing viable progeny, e.g., by about 20%, 40%, 60%, 80%, or more. The effect may be apparent either immediately or in successive generations, or both.

The nematicidal compositions described herein can be used to treat diseases or infestations caused by nematodes of the following non-limiting, exemplary genera: *Anguina, Ditylenchus, Tylenchorhynchus, Pratylenchus, Radopholus, Hirschmanniella, Nacobbus, Hoplolaimus, Scutellonema, Rotylenchus, Helicotylenchus, Rotylenchulus, Belonolaimus, Heterodera,* other cyst nematodes, *Meloidogyne, Criconemoides, Hemicycliophora, Paratylenchus, Tylenchulus, Aphelenchoides, Bursaphelenchus, Rhadinaphelenchus, Longidorus, Xiphinema, Trichodorus,* and *Paratrichodorus, Dirofilaria, Onchocerca, Brugia, Acanthocheilonema, Aelurostrongylus, Anchlostoma, Angiostrongylus, Ascaris, Bunostomum, Capillaria, Chabertia, Cooperia, Crenosoma, Dictyocaulus, Dioctophyme, Dipetalonema, Dracunculus, Enterobius, Filaroides, Haemonchus, Lagochilascaris, Loa, Manseonella, Muellerius, Necator, Nematodirus, Oesophagostomum, Ostertagia, Parafilaria, Parascaris, Physaloptera, Protostrongylus, Setaria, Spirocerca, Stephanogilaria, Strongyloides, Strongylus, Thelazia, Toxascaris, Toxocara, Trichinella, Trichostrongylus, Trichuris, Uncinaria,* and *Wuchereria*. In some embodiments, the nematicidal compositions described herein are used to treat diseases or infestations caused by nematodes including *Dirofilaria, Onchocerca, Brugia, Acanthocheilonema, Dipetalonema, Loa, Mansonella, Parafilaria, Setaria, Stephanofilaria, Wucheria, Pratylenchus, Heterodera, Meloidogyne,* and *Paratylenchus*. Examples of non-limiting species include: *Ancylostoma caninum, Haemonchus contortus, Trichinella spiralis, Trichurs muris, Dirofilaria immitis, Dirofilaria tenuis, Dirofilaria repens, Dirofilari ursi, Ascaris suum, Toxocara canis, Toxocara cati, Strongyloides ratti, Parastrongyloides trichosuri, Heterodera glycines, Globodera pallida, Meloidogyne javanica, Meloidogyne incognita,* and *Meloidogyne arenaria, Radopholus similis, Longidorus elongatus, Meloidogyne hapla,* and *Pratylenchus penetrans*.

Having described various embodiments in detail, it will be apparent that modifications and variations are possible without departing from the scope of the invention defined in the appended claims.

EXAMPLES

The following non-limiting examples are provided to further illustrate the disclosure.

Example 1

Nematicidal Efficacy Assay

A miniaturized greenhouse assay was conducted to study the effects of several 3,5-disubstituted-4,5-dihydro-1,2,4-oxadiazoles on *Meloidogyne incognita* nematodes.

Cucumber seeds were sprouted for 3 days in moist paper towels. Acceptable sprouts were 3 to 4 cm long, with several lateral roots just emerging. For each trial compound, a test solution was prepared in a mixture of acetone (500 mL) and TRITON X100 surfactant (412 mg), such that the concentration of the nematicidal test compound was 5 mg/mL. The chemical stock solution was then added to a mixture of deionized water (10 mL) and TRITON X100 (0.015% concentration), and mixed thoroughly.

Each test solution was evaluated in triplicate. Dry sand (10 mL) was added to each vial. Seedlings were planted by tilting the vial and laying the seedling in the correct orientation so that the cotyledons were just above the sand, and then tilting back to cover the radicles with sand.

A sample of the test solution (3.3 mL) was then added to each vial, and the vials were placed in racks under fluorescent light banks. The vials were inoculated two days after planting by adding 500 vermiform *M. incognita* eggs to each vial in deionized or spring water (50 μL). The vials were then kept under the fluorescent lamps at ambient room temperature and watered as needed with deionized water (1 mL), usually twice during duration of test.

Harvest of the cucumber plants was performed 10 to 12 days after inoculation by washing sand off the roots. A root gall rating was assigned using the following Gall rating scale (Gall: % root mass galled): 0=0-5%; 1=6-20%; 2=21-50%; and 3=51-100%. For each test solution, the average of the triplicate gall ratings was then calculated and scored: no galls=0.00-0.33; mild galling=0.67-1.33; moderate galling=1.67-2.33; severe galling=2.67-3.00.

Other commercially available nematicidal compounds were also evaluated as controls.

TABLE 1A

Examples of 3,5-disubstituted-4,5-dihydro-1,2,4-oxadiazoles with their nematicidal activity, and comparison to commercial standards

| Formula | Name | Structure | 8/1/0.5 ppm gall ratings* |
|---|---|---|---|
| Ia-i | 3-phenyl-5-(thiophen-2-yl)-4,5-dihydro-1,2,4-oxadiazole | 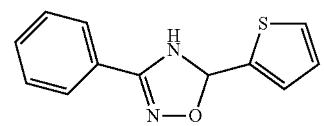 [SMILES: c1ccc(C2=NOC(c3cccs3)N2)cc1] | $0.00^a/1.33^a/2.33^a$; $0.00^b/1.67^b/2.67^b$ |
| Ia-ii | 5-(furan-2-yl)-3-phenyl-4,5-dihydro-1,2,4-oxadiazole | 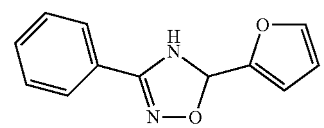 [SMILES: c1ccc(C2=NOC(c3ccco3)N2)cc1] | $0.00^a/2.00^a/2.67^a$; $0.00^b/0.67^b/2.33^b$ |
| Ia-iii | 3-(4-chlorophenyl)-5-(furan-2-yl)-4,5-dihydro-1,2,4-oxadiazole | 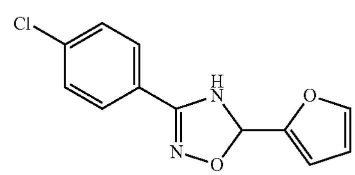 [SMILES: Clc1ccc(C2=NOC(c3ccco3)N2)cc1] | $0.00^b/1.67^b/3.00^b$ |
| Ia-iv | 3-(4-chloro-2-methylphenyl)-5-(furan-2-yl)-4,5-dihydro-1,2,4-oxadiazole | 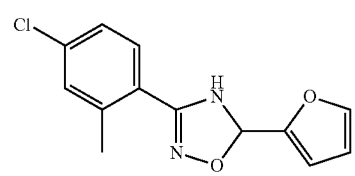 [SMILES: Cc1cc(Cl)ccc1C1=NOC(c2ccco2)N1] | $0.00^b/1.67^b/2.67^b$ |
| Ia-v | 3-(4-fluorophenyl)-5-(thiophen-2-yl)-4,5-dihydro-1,2,4-oxadiazole | 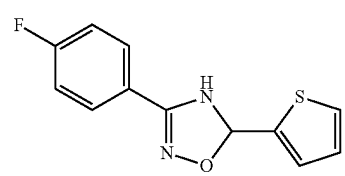 [SMILES: Fc1ccc(C2=NOC(c3cccs3)N2)cc1] | $0.00^b/0.00^b/1.67^b$ |
| Ib-iv | 3-(4-chlorophenyl)-5-(furan-3-yl)-4,5-dihydro-1,2,4-oxadiazole | 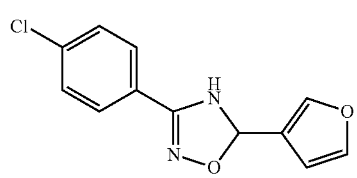 [SMILES: Clc1ccc(C2=NOC(c3ccoc3)N2)cc1] | $0.00^b/1.33^b/2.67^b$ |
| Ia-ix | 3-(2,4-dichlorophenyl)-5-(furan-2-yl)-4,5-dihydro-1,2,4-oxadiazole | 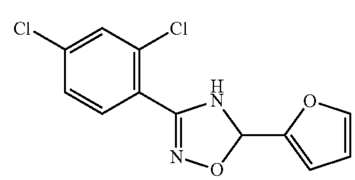 [SMILES: Clc1ccc(C2=NOC(c3ccco3)N2)c(Cl)c1] | $0.00^b/2.33^b/3.00^b$ |

TABLE 1A-continued

Examples of 3,5-disubstituted-4,5-dihydro-1,2,4-oxadiazoles with their nematicidal activity, and comparison to commercial standards

| Formula | Name | Structure | 8/1/0.5 ppm gall ratings* |
|---|---|---|---|
| IIa-iii | 5-(4-chloro-2-methylphenyl)-3-(furan-2-yl)-4,5-dihydro-1,2,4-oxadiazole | 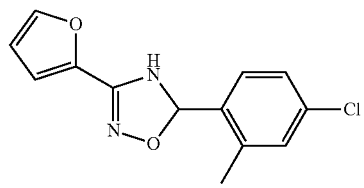 [SMILES: Cc1cc(Cl)ccc1C1NC(c2ccco2)=NO1] | $0.00^b/1.67^b/2.33^b$ |
| IIa-ii | 5-(3-chlorophenyl)-3-(thiophen-2-yl)-4,5-dihydro-1,2,4-oxadiazole | 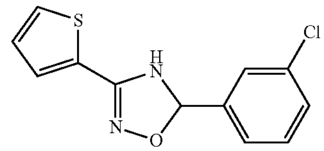 [SMILES: Clc1cccc(C2NC(c3cccs3)=NO2)c1] | $0.33^b/2.33^b/3.00^b$ |
| | Fenamiphos (1 ppm) | | $0.00^a; 0.00^b$ |
| | Vydate (1 ppm) | | $1.67^a; 1.00^b$ |
| | Abamectin (1 ppm) | | $1.67^a$ |

*Data with the same letters were taken from the same test

Example 2

Description of Synthesis of the Compounds of Formulas I and II

The compounds of Formula I and Formula II may be prepared using methods known to those skilled in the art. In general, 3,5-substituted-4,5-dihydro-1,2,4-oxadiazoles are prepared by reacting an appropriate aldehyde with a corresponding amidoxime at elevated temperature in a solvent or without solvent in the presence of a catalyst. More specifically, the compounds of Formulas Ia and Ib can be prepared as illustrated by exemplary Scheme I.

As shown in Scheme I below, the optionally substituted benzamidoxime 1 is reacted with the corresponding heteroaryl carboxaldehyde 2, in toluene in the presence of 3 Angstrom molecular sieves and catalytic piperidine at 100° C., to yield the desired 3,5-disubstituted-4,5-dihydro-1,2,4-oxadiazole 3. Substituent X corresponds to substituents $R_1$ through $R_5$ as defined with respect to Formulas Ia and Ib above. Substituent Y is thienyl or furanyl, optionally substituted with substituents $R_6$, $R_7$, $R_8$, and/or $R_9$ as described with respect to Formulas Ia and Ib above.

Scheme I: Synthetic route to compounds of the Formula I

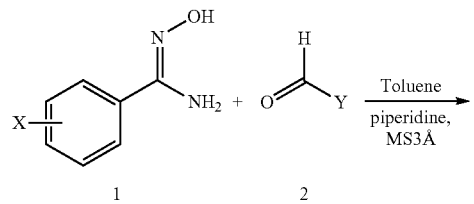

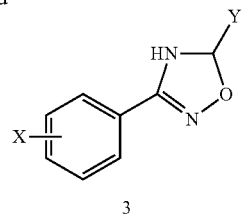

Similarly, the compounds of Formulas IIa and IIb may be prepared as illustrated by exemplary Scheme 2, shown below. Substituent X corresponds to substituents $R_1$ through $R_5$ as defined with respect to Formulas IIa and IIb above. Substituent Y is thienyl or furanyl, optionally substituted with substituents $R_6$, $R_7$, $R_8$, and/or $R_9$ as described with respect to Formulas IIa and IIb above.

Scheme II: Synthetic route to compounds of the Formula II

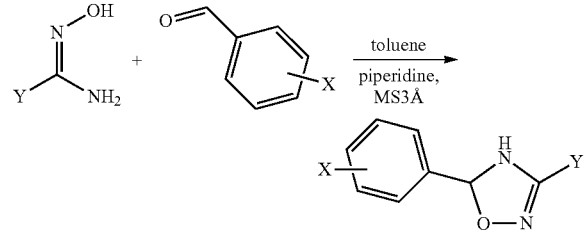

Example 3

Preparation of 3-phenyl-5-(thiophen-2-yl)-4,5-dihydro-1,2,4-oxadiazole, Formula Ia-i A mixture of 2-thiophenecarboxaldehyde (77 mL, 92.6 g, 826 mmol, 1.5 equivalents), N'-hydroxybenzimidamide (75.0 mL, 50 mmol) and piperidine (3.8 mL) in toluene (1400 mL)

was heated to reflux for 30 hours in a SOXHLETT apparatus that was charged with SILCARBON 3 Angstrom molecular sieve (200 g). The reaction mixture was allowed to cool to room temperature, and heptane (1 L) was added. A thick, oily solid was then separated from the reaction mixture by decantation. After the remaining reaction mixture was left standing for 1 hour, it was observed that additional solid had precipitated from the mixture, and this precipitate was separated by decantation as well.

The combined solids were purified using column chromatography (SiO$_2$, gradient heptane/ethyl acetate=4/1). The appropriate fractions were combined and concentrated in vacuo until approximately 250 mL of heptanes were remaining. At that point, solid 3-phenyl-5-(thiophen-2-yl)-4,5-dihydro-1,2,4-oxadiazole product precipitated. After standing for one night at room temperature, the solid product was filtered off and washed with heptane (1 L). The product was dried in vacuo to give 3-phenyl-5-(thiophen-2-yl)-4,5-dihydro-1,2,4-oxadiazole (34.0 g, 169 mmol) as a slightly orange solid. The overall reaction yield was 31%. Liquid chromatography-mass spectrometry (LC-MS) [M+H] 231 (C$_{12}$H$_{10}$N$_2$OS+H, expected 231.05).

Example 4

Preparation of 5-(furan-2-yl)-3-phenyl-4,5-dihydro-1,2,4-oxadiazole, Formula Ia-ii A mixture of 2-furfural (1.0 mL, 1.17 g, 12.2 mmol, 1.5 equivalents), N'-hydroxybenzimidamide (1.11 g, 8.1 mmol) and one drop of piperidine in toluene (100 mL) was heated to reflux for 18 hours in a SOXHLETT apparatus that was charged with SILCARBON 3 Angstrom molecular sieve (8 g). The reaction mixture was allowed to cool to room temperature, and the solvent was removed in vacuo. After purification by automated column chromatography on an ISCO COMPANION apparatus (SiO$_2$, gradient heptane/ethyl acetate), the 5-(furan-2-yl)-3-phenyl-4,5-dihydro-1,2,4-oxadiazole product (745 mg, 3.5 mmol) was obtained as a brown oil that solidified to a tan solid upon standing. The overall reaction yield was approximately 43%. LC-MS [M+H] 215 (C$_{12}$H$_{10}$N$_2$O$_2$+H, expected 215.07].

Example 5

Preparation of 3-(4-chlorophenyl)-5-(furan-2-yl)-4,5-dihydro-1,2,4-oxadiazole, Formula Ia-iii A mixture of 2-furfural (0.69 mL, 804 mg, 8.4 mmol), 4-chloro-N'-hydroxybenzimidamide (1.02 g, 6.0 mmol) and one drop of piperidine in toluene (100 mL) was heated to reflux for 18 h in a Soxhlett apparatus, that was charged with 3 Angstrom molecular sieves (8 g). The mixture was cooled to room temperature and the solvent was removed in vacuo. After purification by automated column chromatography on the ISCO COMPANION (SiO$_2$, gradient heptane/ethyl acetate) the 3-(4-chlorophenyl)-5-(furan-2-yl)-4,5-dihydro-1,2,4-oxadiazole product was obtained as an orange oil that solidified to a tan solid upon standing (85 mg) with a yield of 6%. LC-MS [M+H] 249 (C$_{12}$H$_9$ClN$_2$O$_2$+H, expected 249.04)

Example 6

Preparation of 3-(4-chloro-2-methylphenyl)-5-(furan-2-yl)-4,5-dihydro-1,2,4-oxadiazole, Formula Ia-iv A mixture of 2-furancarboxaldehyde (166 mL, 192 mg, 2.0 mmol), 4-chloro-N'-hydroxy-2-methylbenzimidamide (368 mg, 2.0 mmol) and one drop of piperidine was heated to 10° C. for 4 h. The mixture was cooled to room temperature and purified by automated column chromatography on the ISCO COMPANION (SiO$_2$, gradient heptanes/ethyl acetate) to give the 3-(4-chloro-2-methylphenyl)-5-(furan-2-yl)-4,5-dihydro-1,2,4-oxadiazole product (95 mg) with a yield of 18%. LC-MS [M+H] 263 (C$_{13}$H$_{11}$ClN$_2$O$_2$+H, expected 263.05)

Example 7

Preparation of 3-(4-fluorophenyl)-5-(thiophen-2-yl)-4,5-dihydro-1,2,4-oxadiazole, Formula Ia-v A mixture of 4-fluoro-N'-hydroxybenzimidamide (230 mg, 1.49 mmol), 2-thiophenecarboxyaldehyde (234 mg, 2.09 mmol), and one drop of piperidine in toluene was heated to reflux according to the procedure as described for Example 3 and after purification the 3-(4-fluorophenyl)-5-(thiophen-2-yl)-4,5-dihydro-1,2,4-oxadiazole (149 mg, 0.60 mmol) was obtained as an off-white solid with an HPLC purity of 99%. The overall yield was approximately 40%. LC-MS [M+H] 249 (C$_{12}$H$_9$FN$_2$OS+H, expected 249.04).

Example 8

Preparation of 3-(2,4-dichlorophenyl)-5-(furan-2-yl)-4,5-dihydro-1,2,4-oxadiazole, Formula Ia-ix A mixture of 2,4-dichloro-N'-hydroxybenzimidamide (426 mg, 2.09 mmol), 2-furaldehyde (143 mg, 1.49 mmol) and one drop of piperidine in toluene was heated to reflux according to the procedure as described for Example 3 and after purification the 3-(2,4-dichlorophenyl)-5-(furan-2-yl)-4,5-dihydro-1,2,4-oxadiazole product (52 mg, 0.183 mmol) was obtained as an off-white solid with an HPLC purity of 98.7%. The overall yield was approximately 12%. LC-MS [M+H] 283/285 (C12H8Cl2N2O2+H, expected 283.00/284.99).

Example 9

Preparation of 3-(4-chlorophenyl)-5-(furan-3-yl)-4,5-dihydro-1,2,4-oxadiazole, Formula Ib-iv A mixture of 4-chloro-N'-hydroxy-2-benzimidamide (7, 253 mg, 1.49 mmol), 3-furaldehyde (200 mg, 2.09 mmol) and one drop of piperidine in toluene was heated to reflux according to the procedure as described for Example 3 and after purification the 3-(4-chlorophenyl)-5-(furan-3-yl)-4,5-dihydro-1,2,4-oxadiazole product (23 mg, 0.09 mmol) was obtained as a tan solid with an HPLC purity of 98%. The overall yield was approximately 6%. LC-MS [M+H] 249/250 (C$_{12}$H$_9$ClN$_2$O$_2$+H, expected 248.04/250.04).

Example 10

Preparation of 5-(3-chlorophenyl)-3-(thiophen-2-yl)-4,5-dihydro-1,2,4-oxadiazole, Formula IIa-ii A mixture of N'-hydroxythiophene-2-carboximidamide (212 mg, 1.49 mmol), 4-chlorobenzaldehyde (294 mg, 2.09 mmol) and one drop of piperidine in toluene was heated to reflux according to the procedure as described for Example 3 and after purification the 5-(3-chlorophenyl)-3-(thiophen-2-yl)-4,5-dihydro-1,2,4-oxadiazole product (58 mg, 0.22 mmol) was obtained as an off-white solid with an HPLC purity of 99.5%. The overall yield was approximately 15%.
LC-MS [M+H] 265 ($C_{12}H_9ClN_2OS+H$, expected 265.01).

Example 11

Preparation of 5-(4-chloro-2-methylphenyl)-3-(furan-2-yl)-4,5-dihydro-1,2,4-oxadiazole, Formula IIa-iii A mixture of 4-chloro-2-methylbenzaldehyde (229 mg, 1.49 mmol), N'-hydroxyfuran-2-carboximidamide (263 mg, 2.1 mmol) and one drop of piperidine was heated to 100° C. for 4 h. It was cooled to RT and purified by automated column chromatography on the ISCO-companion ($SiO_2$, gradient heptane/ethyl acetate) to give the 5-(4-chloro-2-methylphenyl)-3-(furan-2-yl)-4,5-dihydro-1,2,4-oxadiazole product (94 mg, 0.36 mmol) as an off-white solid with an HPLC purity 99%. The overall yield was approximately 24%. LC-MS [M+H] 263 ($C_{13}H_{11}ClN_2O_2+H$, expected 263.05).

When introducing elements of the disclosure or exemplary embodiments, the articles "a", "an", "the" and "said" are intended to mean that there are one or more of the elements. The terms "comprising", "including" and "having" are intended to be inclusive and mean that there may be additional elements other than the listed elements.

As various changes could be made in the above products and methods without departing from the scope of the invention, it is intended that all matter contained in the above description shall be interpreted as illustrative and not in a limiting sense.

What is claimed is:

1. A compound of Formula I, Formula II, or a salt thereof,

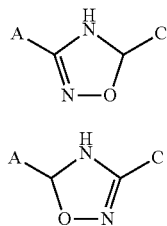

Formula I

Formula II wherein A is selected from the group consisting of phenyl, pyridyl, pyrazyl, oxazolyl and isoxazolyl, each of which can be optionally independently substituted with one or more substituents selected from the group consisting of halogen, $CF_3$, $CH_3$, $OCF_3$, $OCH_3$, CN, and C(H)O; and C is selected from the group consisting of thienyl, furanyl, isoxazolyl, pyrrolyl, and pyrrolidinyl, each of which can be optionally independently substituted with one or more substituents selected from the group consisting of alkyl, alkoxy, cycloalkyl, haloalkyl, haloalkoxy, heterocyclyl, and halogen.

2. The compound of claim 1 wherein A is optionally independently substituted phenyl.

3. The compound of claim 1 wherein C is optionally independently substituted pyrrolyl.

4. The compound of claim 1 wherein C is optionally independently substituted thienyl.

5. The compound of claim 1 wherein C is optionally independently substituted furanyl.

6. The compound of claim 1 wherein the compound is of Formula Ia or a salt thereof,

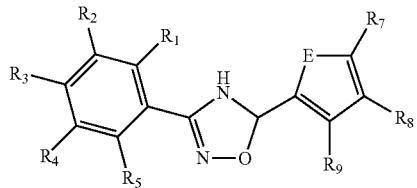

Formula Ia wherein $R_1$ and $R_5$ are independently selected from the group consisting of hydrogen, $CH_3$, F, Cl, Br, $CF_3$ and $OCF_3$;

$R_2$ and $R_4$ are independently selected from the group consisting of hydrogen, F, Cl, Br, and $CF_3$;

$R_3$ is selected from the group consisting of hydrogen, $CH_3$, $CF_3$, F, Cl, Br, $OCF_3$, $OCH_3$, CN, and C(H)O;

$R_7$, $R_8$ and $R_9$ are selected from the group consisting of hydrogen, alkyl, alkoxy, cycloalkyl, haloalkyl, haloalkoxy, heterocyclyl, and halogen; and E is selected from the group consisting of O, S, and N—$R_{10}$, wherein $R_{10}$ is alkyl.

7. The compound of claim 1 wherein the compound is of Formula Ib or a salt thereof,

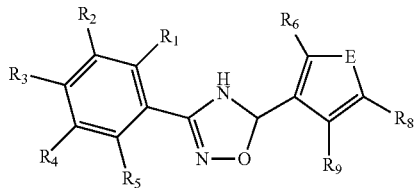

Formula Ib wherein $R_1$ and $R_5$ are independently selected from the group consisting of hydrogen, $CH_3$, F, Cl, Br, $CF_3$ and $OCF_3$;

$R_2$ and $R_4$ are independently selected from the group consisting of hydrogen, F, Cl, Br, and $CF_3$;

$R_3$ is selected from the group consisting of hydrogen, $CH_3$, $CF_3$, F, Cl, Br, $OCF_3$, $OCH_3$, CN, and C(H)O;

$R_6$, $R_8$ and $R_9$ are selected from the group consisting of hydrogen, alkyl, alkoxy, cycloalkyl, haloalkyl, haloalkoxy, heterocyclyl, and halogen; and E is selected from the group consisting of O, S, and N—$R_{10}$, wherein $R_{10}$ is alkyl.

8. The compound of claim 1 wherein the compound is of Formula Ic or a salt thereof,

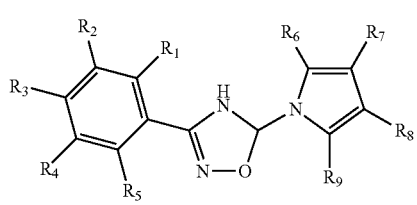

Formula Ic wherein $R_1$ and $R_5$ are independently selected from the group consisting of hydrogen, $CH_3$, F, Cl, Br, $CF_3$ and $OCF_3$;

$R_2$ and $R_4$ are independently selected from the group consisting of hydrogen, F, Cl, Br and $CF_3$;

R₃ is selected from the group consisting of hydrogen, CH₃, CF₃, F, Cl, Br, OCF₃, OCH₃, CN, and C(H)O; and R₆, R₇, R₈ and R₉ are selected from the group consisting of hydrogen, alkyl, alkoxy, cycloalkyl, haloalkyl, haloalkoxy, heterocyclyl, and halogen.

9. The compound of claim 1 wherein the compound is of Formula IIa or a salt thereof,

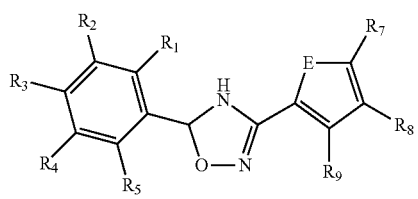

Formula IIa wherein R₁ and R₅ are independently selected from the group consisting of hydrogen, CH₃, F, Cl, Br, CF₃ and OCF₃;

R₂ and R₄ are independently selected from the group consisting of hydrogen, F, Cl, Br, and CF₃;

R₃ is selected from the group consisting of hydrogen, CH₃, CF₃, F, Cl, Br, OCF₃, OCH₃, CN, and C(H)O;

R₇, R₈ and R₉ are selected from the group consisting of hydrogen, alkyl, alkoxy, cycloalkyl, haloalkyl, haloalkoxy, heterocyclyl, and halogen; and E is selected from the group consisting of O, S, and N—R₁₀, wherein R₁₀ is alkyl.

10. The compound of claim 1 wherein the compound is of Formula IIb or a salt thereof,

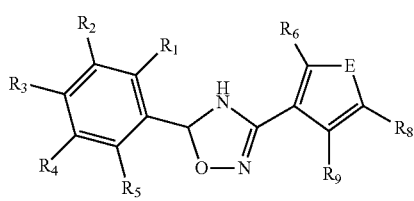

Formula IIb wherein R₁ and R₅ are independently selected from the group consisting of hydrogen, CH₃, F, Cl, Br, CF₃ and OCF₃;

R₂ and R₄ are independently selected from the group consisting of hydrogen, F, Cl, Br, and CF₃;

R₃ is selected from the group consisting of hydrogen, CH₃, CF₃, F, Cl, Br, OCF₃, OCH₃, CN, and C(H)O;

R₆, R₈ and R₉ are selected from the group consisting of hydrogen, alkyl, alkoxy, cycloalkyl, haloalkyl, haloalkoxy, heterocyclyl, and halogen; and E is selected from the group consisting of O, S, and N—R₁₀, wherein R₁₀ is alkyl.

11. The compound of claim 1 wherein the compound is of Formula IIc or a salt thereof,

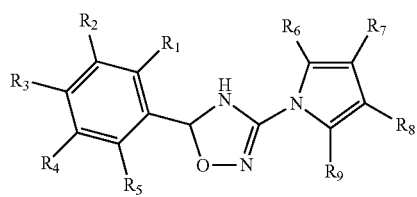

Formula IIc wherein R₁ and R₅ are independently selected from the group consisting of hydrogen, CH₃, F, Cl, Br, CF₃ and OCF₃;

R₂ and R₄ are independently selected from the group consisting of hydrogen, F, Cl, Br and CF₃;

R₃ is selected from the group consisting of hydrogen, CH₃, CF₃, F, Cl, Br, OCF₃, OCH₃, CN, and C(H)O; and R₆, R₇, R₈ and R₉ are selected from the group consisting of hydrogen, alkyl, alkoxy, cycloalkyl, haloalkyl, haloalkoxy, heterocyclyl, and halogen.

12. A compound of claim 1 wherein A is substituted phenyl and C is selected from the group consisting of optionally independently substituted pyrrolyl, thienyl, and furanyl.

13. A compound selected from the group consisting of:
3-phenyl-5-(thiophen-2-yl)-4,5-dihydro-1,2,4-oxadiazole, or a salt thereof;
5-(furan-2-yl)-3-phenyl-4,5-dihydro-1,2,4-oxadiazole, or a salt thereof;
3-(4-chlorophenyl)-5-(furan-2-yl)-4,5-dihydro-1,2,4-oxadiazole, or a salt thereof;
3-(4-chloro-2-methylphenyl)-5-(furan-2-yl)-4,5-dihydro-1,2,4-oxadiazole, or a salt thereof;
3-(4-fluorophenyl)-5-(thiophen-2-yl)-4,5-dihydro-1,2,4-oxadiazole, or a salt thereof;
3-(4-chlorophenyl)-5-(thiophen-2-yl)-4,5-dihydro-1,2,4-oxadiazole, or a salt thereof;
3-(4-bromophenyl)-5-(thiophen-2-yl)-4,5-dihydro-1,2,4-oxadiazole, or a salt thereof;
3-(4-bromophenyl)-5-(furan-2-yl)-4,5-dihydro-1,2,4-oxadiazole, or a salt thereof;
3-(2,4-dichlorophenyl)-5-(furan-2-yl)-4,5-dihydro-1,2,4-oxadiazole, or a salt thereof;
3-(4-bromophenyl)-5-(furan-3-yl)-4,5-dihydro-1,2,4-oxadiazole, or a salt thereof;
3-(2,4-difluorophenyl)-5-(thiophen-3-yl)-4,5-dihydro-1,2,4-oxadiazole, or a salt thereof;
3-(4-chlorophenyl)-5-(thiophen-3-yl)-4,5-dihydro-1,2,4-oxadiazole, or a salt thereof;
3-(4-chlorophenyl)-5-(furan-3-yl)-4,5-dihydro-1,2,4-oxadiazole, or a salt thereof;
3-(4-fluorophenyl)-5-(thiophen-3-yl)-4,5-dihydro-1,2,4-oxadiazole, or a salt thereof;
3-(4-fluorophenyl)-5-(furan-3-yl)-4,5-dihydro-1,2,4-oxadiazole, or a salt thereof;
3-(4-fluorophenyl)-5-(furan-3-yl)-4,5-dihydro-1,2,4-oxadiazole, or a salt thereof;
5-phenyl-3-(1H-pyrrol-1-yl)-4,5-dihydro-1,2,4-oxadiazole, or a salt thereof;
3-(thiophen-2-yl)-5-(p-tolyl)-4,5-dihydro-1,2,4-oxadiazole, or a salt thereof;
5-(3-chlorophenyl)-3-(thiophen-2-yl)-4,5-dihydro-1,2,4-oxadiazole, or a salt thereof;
5-(4-chloro-2-methylphenyl)-3-(furan-2-yl)-4,5-dihydro-1,2,4-oxadiazole, or a salt thereof;
5-phenyl-3-(thiophen-3-yl)-4,5-dihydro-1,2,4-oxadiazole, or a salt thereof; and 3-phenyl-5-(1H-pyrrol-1-yl)-4,5-dihydro-1,2,4-oxadiazole, or a salt thereof.

14. The compound of claim 13 wherein the compound is selected from the group consisting of:
 3-phenyl-5-(thiophen-2-yl)-4,5-dihydro-1,2,4-oxadiazole, or a salt thereof,
 5-(furan-2-yl)-3-phenyl-4,5-dihydro-1,2,4-oxadiazole, or a salt thereof,
 3-(4-chlorophenyl)-5-(furan-2-yl)-4,5-dihydro-1,2,4-oxadiazole, or a salt thereof,
 3-(4-chloro-2-methylphenyl)-5-(furan-2-yl)-4,5-dihydro-1,2,4-oxadiazole, or a salt thereof;
 3-(4-fluorophenyl)-5-(thiophen-2-yl)-4,5-dihydro-1,2,4-oxadiazole
 3-(2,4-dichlorophenyl)-5-(furan-2-yl)-4,5-dihydro-1,2,4-oxadiazole
 3-(4-chlorophenyl)-5-(furan-3-yl)-4,5-dihydro-1,2,4-oxadiazole
 5-(3-chlorophenyl)-3-(thiophen-2-yl)-4,5-dihydro-1,2,4-oxadiazole; and
 5-(4-chloro-2-methylphenyl)-3-(furan-2-yl)-4,5-dihydro-1,2,4-oxadiazole.

15. The compound of claim 14 wherein the compound is 3-phenyl-5-(thiophen-2-yl)-4,5-dihydro-1,2,4-oxadiazole, or a salt thereof.

16. An aqueous nematicidal composition comprising the compound of claim 1.

17. The nematicidal composition of claim 16 further comprising a surfactant.

18. The nematicidal composition of claim 16 further comprising a co-solvent.

19. The nematicidal composition of claim 16 further comprising a biological control agent, microbial extract, plant growth activator or plant defense agent or mixtures thereof.

20. The nematicidal composition of claim 19 wherein the biological control agent is a plant growth activator or plant defense agent selected from the group consisting of harpin, *Reynoutria sachalinensis*, jasmonate, lipochitooligosaccharides, and isoflavones.

21. The nematicidal composition of claim 16 further comprising a second pesticide.

22. The nematicidal composition of claim 21 wherein the second pesticide is selected from the group consisting of fungicides, insecticides and herbicides or mixtures thereof.

23. The nematicidal composition of claim 21 wherein the second pesticide is selected from the group consisting of fluxapyroxad, ipconazole, metalaxyl, penflufen, pyraclostrobin, trifloxystrobin, abamectin, *Bacillus firmus*, clothianidin, imidacloprid, thiamethoxam and mixtures thereof.

24. A seed comprising a coating comprising a compound of claim 1.

25. A method of controlling unwanted nematodes, the method comprising administering to a plant, a seed, or soil a composition comprising an effective amount of a compound of claim 1.

26. The compound of claim 1 wherein C is optionally independently substituted with one or more substituents selected from the group consisting of F, Cl, CH₃, CF₃, Br, OCH₃, and OCF₃.

27. A method of controlling unwanted nematodes, the method comprising administering to a plant, a seed, or soil a composition comprising an effective amount of a compound of Formula I, Formula II, or a salt thereof,

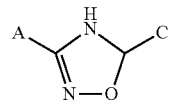

Formula I

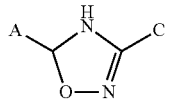

Formula II wherein A is selected from the group consisting of phenyl, pyridyl, pyrazyl, oxazolyl and isoxazolyl, each of which can be optionally independently substituted with one or more substituents selected from the group consisting of halogen, CF₃, CH₃, OCF₃, OCH₃, CN, and C(H)O; and
C is selected from the group consisting of thienyl, furanyl, oxazolyl, isoxazolyl, pyrrolyl, and pyrrolidinyl, each of which can be optionally independently substituted with one or more substituents selected from the group consisting of alkyl, alkoxy, cycloalkyl, haloalkyl, haloalkoxy, heterocyclyl, and halogen.

28. The method of claim 27 wherein A is optionally independently substituted phenyl.

29. The method of claim 27 wherein C is optionally independently substituted pyrrolyl.

30. The method of claim 27 wherein C is optionally independently substituted thienyl.

31. The method of claim 27 wherein C is optionally independently substituted furanyl.

32. The method of claim 27 wherein the compound is of Formula Ia or a salt thereof,

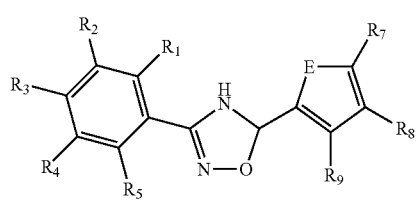

Formula Ia wherein R₁ and R₅ are independently selected from the group consisting of hydrogen, CH₃, F, Cl, Br, CF₃ and OCF₃;
R₂ and R₄ are independently selected from the group consisting of hydrogen, F, Cl, Br, and CF₃;
R₃ is selected from the group consisting of hydrogen, CH₃, CF₃, F, Cl, Br, OCF₃, OCH₃, CN, and C(H)O;
R₇, R₈ and R₉ are selected from the group consisting of hydrogen, alkyl, alkoxy, cycloalkyl, haloalkyl, haloalkoxy, heterocyclyl, and halogen; and
E is selected from the group consisting of O, S, and N—R₁₀, wherein R₁₀ is alkyl.

33. The method of claim 32 wherein R₇, R₈, and R₉ are independently selected from the group consisting of hydrogen, F, Cl, CH3, and OCF₃.

34. The method of claim 27 wherein the compound is of Formula Ib or a salt thereof,

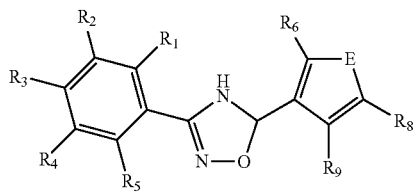

Formula Ib wherein R₁ and R₅ are independently selected from the group consisting of hydrogen, CH₃, F, Cl, Br, CF₃ and OCF₃;

R₂ and R₄ are independently selected from the group consisting of hydrogen, F, Cl, Br, and CF₃;

R₃ is selected from the group consisting of hydrogen, CH₃, CF₃, F, Cl, Br, OCF₃, OCH₃, CN, and C(H)O;

R₆, R₈ and R₉ are selected from the group consisting of hydrogen, alkyl, alkoxy, cycloalkyl, haloalkyl, haloalkoxy, heterocyclyl, and halogen; and E is selected from the group consisting of O, S, and N—R₁₀, wherein R₁₀ is alkyl.

35. The method of claim 27 wherein the compound is of Formula Ic or a salt thereof,

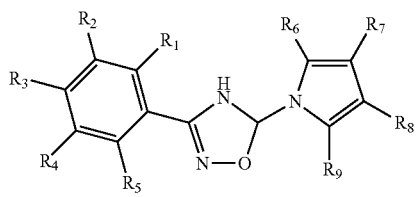

Formula Ic wherein R₁ and R₅ are independently selected from the group consisting of hydrogen, CH₃, F, Cl, Br, CF₃ and OCF₃;

R₂ and R₄ are independently selected from the group consisting of hydrogen, F, Cl, Br and CF₃;

R₃ is selected from the group consisting of hydrogen, CH₃, CF₃, F, Cl, Br, OCF₃, OCH₃, CN, and C(H)O; and R₆, R₇, R₈ and R₉ are selected from the group consisting of hydrogen, alkyl, alkoxy, cycloalkyl, haloalkyl, haloalkoxy, heterocyclyl, and halogen.

36. The method of claim 27 wherein the compound is of Formula IIa or a salt thereof,

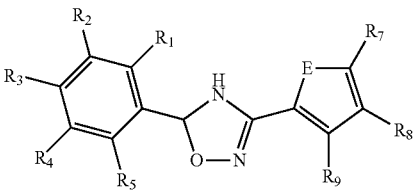

Formula IIa wherein R₁ and R₅ are independently selected from the group consisting of hydrogen, CH₃, F, Cl, Br, CF₃ and OCF₃;

R₂ and R₄ are independently selected from the group consisting of hydrogen, F, Cl, Br, and CF₃;

R₃ is selected from the group consisting of hydrogen, CH₃, CF₃, F, Cl, Br, OCF₃, OCH₃, CN, and C(H)O;

R₇, R₈ and R₉ are selected from the group consisting of hydrogen, alkyl, alkoxy, cycloalkyl, haloalkyl, haloalkoxy, heterocyclyl, and halogen; and E is selected from the group consisting of O, S, and N—R₁₀, wherein R₁₀ is alkyl.

37. The method of claim 36 wherein R₇, R₈, and R₉ are independently selected from the group consisting of hydrogen, F, Cl, CH3, and OCF₃.

38. The method of claim 27 wherein the compound is of Formula IIb or a salt thereof,

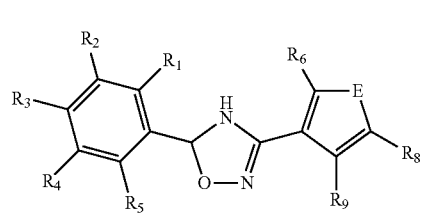

Formula IIb wherein R₁ and R₅ are independently selected from the group consisting of hydrogen, CH₃, F, Cl, Br, CF₃ and OCF₃;

R₂ and R₄ are independently selected from the group consisting of hydrogen, F, Cl, Br, and CF₃;

R₃ is selected from the group consisting of hydrogen, CH₃, CF₃, F, Cl, Br, OCF₃, OCH₃, CN, and C(H)O;

R₆, R₈ and R₉ are selected from the group consisting of hydrogen, alkyl, alkoxy, cycloalkyl, haloalkyl, haloalkoxy, heterocyclyl, and halogen; and E is selected from the group consisting of O, S, and N—R₁₀, wherein R₁₀ is alkyl.

39. The method of claim 27 wherein the compound is of Formula IIc or a salt thereof,

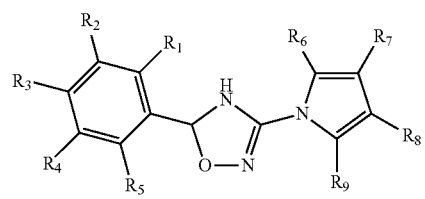

Formula IIc wherein R₁ and R₅ are independently selected from the group consisting of hydrogen, CH₃, F, Cl, Br, CF₃ and OCF₃;

R₂ and R₄ are independently selected from the group consisting of hydrogen, F, Cl, Br and CF₃;

R₃ is selected from the group consisting of hydrogen, CH₃, CF₃, F, Cl, Br, OCF₃, OCH₃, CN, and C(H)O; and R₆, R₇, R₈ and R₉ are selected from the group consisting of hydrogen, alkyl, alkoxy, cycloalkyl, haloalkyl, haloalkoxy, heterocyclyl, and halogen.

40. A treated seed comprising a nematicidal composition comprising an effective amount of a compound of Formula I, Formula II, or a salt thereof,

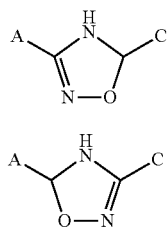

wherein A is selected from the group consisting of phenyl, pyridyl, pyrazyl, oxazolyl and isoxazolyl, each of which can be optionally independently substituted with one or more substituents selected from the group consisting of halogen, $CF_3$, $CH_3$, $OCF_3$, $OCH_3$, CN, and C(H)O; and C is selected from the group consisting of thienyl, furanyl, oxazolyl, isoxazolyl, pyrrolyl, and pyrrolidinyl, each of which can be optionally independently substituted with one or more substituents selected from the group consisting of alkyl, alkoxy, cycloalkyl, haloalkyl, haloalkoxy, heterocyclyl, and halogen.

41. The seed of claim 40 wherein A is optionally independently substituted phenyl.

42. The seed of claim 40 wherein C is optionally independently substituted pyrrolyl.

43. The seed of claim 40 wherein C is optionally independently substituted thienyl.

44. The seed of claim 40 wherein C is optionally independently substituted furanyl.

45. The seed of claim 40 wherein the compound is of Formula Ia or a salt thereof,

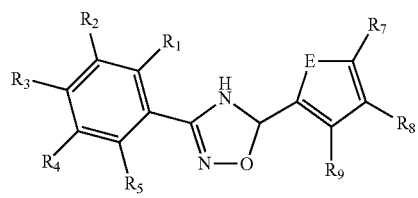

wherein $R_1$ and $R_5$ are independently selected from the group consisting of hydrogen, $CH_3$, F, Cl, Br, $CF_3$ and $OCF_3$;

$R_2$ and $R_4$ are independently selected from the group consisting of hydrogen, F, Cl, Br, and $CF_3$;

$R_3$ is selected from the group consisting of hydrogen, $CH_3$, $CF_3$, F, Cl, Br, $OCF_3$, $OCH_3$, CN, and C(H)O;

$R_7$, $R_8$ and $R_9$ are selected from the group consisting of hydrogen, alkyl, alkoxy, cycloalkyl, haloalkyl, haloalkoxy, heterocyclyl, and halogen; and E is selected from the group consisting of O, S, and N—$R_{10}$, wherein $R_{10}$ is alkyl.

46. The seed of claim 45 wherein $R_7$, $R_8$, and $R_9$ are independently selected from the group consisting of hydrogen, F, Cl, CH3, and $OCF_3$.

47. The seed of claim 40 wherein the compound is of Formula Ib or a salt thereof,

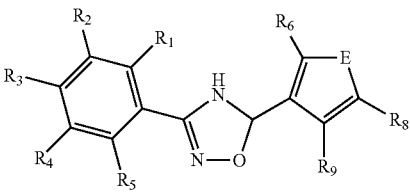

wherein $R_1$ and $R_5$ are independently selected from the group consisting of hydrogen, $CH_3$, F, Cl, Br, $CF_3$ and $OCF_3$;

$R_2$ and $R_4$ are independently selected from the group consisting of hydrogen, F, Cl, Br, and $CF_3$;

$R_3$ is selected from the group consisting of hydrogen, $CH_3$, $CF_3$, F, Cl, Br, $OCF_3$, $OCH_3$, CN, and C(H)O;

$R_6$, $R_8$ and $R_9$ are selected from the group consisting of hydrogen, alkyl, alkoxy, cycloalkyl, haloalkyl, haloalkoxy, heterocyclyl, and halogen; and E is selected from the group consisting of O, S, and N—$R_{10}$, wherein $R_{10}$ is alkyl.

48. The seed of claim 40 wherein the compound is of Formula Ic or a salt thereof,

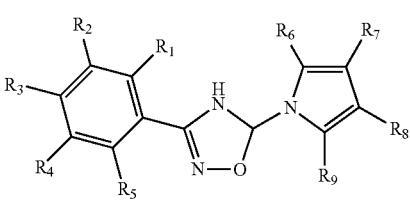

wherein $R_1$ and $R_5$ are independently selected from the group consisting of hydrogen, $CH_3$, F, Cl, Br, $CF_3$ and $OCF_3$;

$R_2$ and $R_4$ are independently selected from the group consisting of hydrogen, F, Cl, Br and $CF_3$;

$R_3$ is selected from the group consisting of hydrogen, $CH_3$, $CF_3$, F, Cl, Br, $OCF_3$, $OCH_3$, CN, and C(H)O; and $R_6$, $R_7$, $R_8$ and $R_9$ are selected from the group consisting of hydrogen, alkyl, alkoxy, cycloalkyl, haloalkyl, haloalkoxy, heterocyclyl, and halogen.

49. The seed of claim 40 wherein the compound is of Formula IIa or a salt thereof,

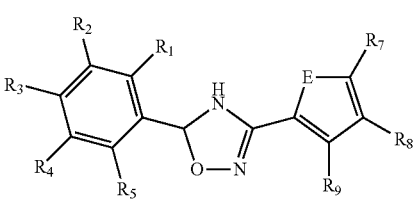

wherein $R_1$ and $R_5$ are independently selected from the group consisting of hydrogen, $CH_3$, F, Cl, Br, $CF_3$ and $OCF_3$;

$R_2$ and $R_4$ are independently selected from the group consisting of hydrogen, F, Cl, Br, and $CF_3$;

$R_3$ is selected from the group consisting of hydrogen, $CH_3$, $CF_3$, F, Cl, Br, $OCF_3$, $OCH_3$, CN, and C(H)O;

$R_7$, $R_8$ and $R_9$ are selected from the group consisting of hydrogen, alkyl, alkoxy, cycloalkyl, haloalkyl, haloalkoxy, heterocyclyl, and halogen; and E is selected from the group consisting of O, S, and N—$R_{10}$, wherein $R_{10}$ is alkyl.

50. The method of claim 49 wherein $R_7$, $R_8$, and $R_9$ are independently selected from the group consisting of hydrogen, F, Cl, CH3, and $OCF_3$.

51. The seed of claim 40 wherein the compound is of Formula IIb or a salt thereof,

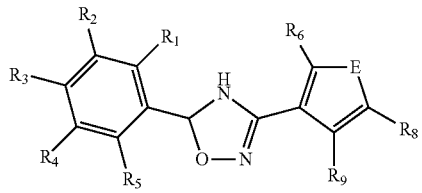

Formula IIb wherein $R_1$ and $R_5$ are independently selected from the group consisting of hydrogen, $CH_3$, F, Cl, Br, $CF_3$ and $OCF_3$;

$R_2$ and $R_4$ are independently selected from the group consisting of hydrogen, F, Cl, Br, and $CF_3$;

$R_3$ is selected from the group consisting of hydrogen, $CH_3$, $CF_3$, F, Cl, Br, $OCF_3$, $OCH_3$, CN, and C(H)O;

$R_6$, $R_8$ and $R_9$ are selected from the group consisting of hydrogen, alkyl, alkoxy, cycloalkyl, haloalkyl, haloalkoxy, heterocyclyl, and halogen; and E is selected from the group consisting of O, S, and N—$R_{10}$, wherein $R_{10}$ is alkyl.

52. The seed of claim 40 wherein the compound is of Formula IIc or a salt thereof,

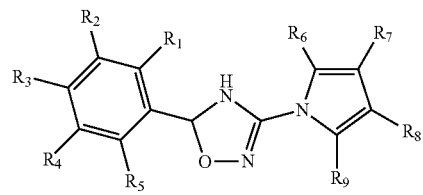

Formula IIc wherein $R_1$ and $R_5$ are independently selected from the group consisting of hydrogen, $CH_3$, F, Cl, Br, $CF_3$ and $OCF_3$;

$R_2$ and $R_4$ are independently selected from the group consisting of hydrogen, F, Cl, Br and $CF_3$;

$R_3$ is selected from the group consisting of hydrogen, $CH_3$, $CF_3$, F, Cl, Br, $OCF_3$, $OCH_3$, CN, and C(H)O; and $R_6$, $R_7$, $R_8$ and $R_9$ are selected from the group consisting of hydrogen, alkyl, alkoxy, cycloalkyl, haloalkyl, haloalkoxy, heterocyclyl, and halogen.

53. A method of controlling unwanted nematodes, the method comprising administering to a plant, a seed, or soil a composition comprising an effective amount of a compound of claim 13.

54. A treated seed comprising a nematicidal composition comprising an effective amount of a compound of claim 13.

* * * * *